US008680336B2

United States Patent
Park et al.

(10) Patent No.: US 8,680,336 B2
(45) Date of Patent: Mar. 25, 2014

(54) DYES FOR DYE SENSITIZED SOLAR CELL

(75) Inventors: Jonghyun Park, Seoul (KR); Seongkee Park, Goyang-si (KR); Sunghoon Joo, Gunpo-si (KR); Jinok Hwang, Seoul (KR); Taeyoun Kim, Seoul (KR)

(73) Assignee: LG Display Co., Ltd., Seoul (KR)

( * ) Notice: Subject to any disclaimer, the term of this patent is extended or adjusted under 35 U.S.C. 154(b) by 855 days.

(21) Appl. No.: 12/585,505

(22) Filed: Sep. 16, 2009

(65) Prior Publication Data
US 2010/0126563 A1 May 27, 2010

(30) Foreign Application Priority Data

Nov. 25, 2008 (KR) .................. 10-2008-0117585
Nov. 25, 2008 (KR) .................. 10-2008-0117601

(51) Int. Cl.
*C07C 211/00* (2006.01)
*C07D 333/22* (2006.01)

(52) U.S. Cl.
USPC ........................................... 564/305; 549/77

(58) Field of Classification Search
None
See application file for complete search history.

(56) References Cited

FOREIGN PATENT DOCUMENTS

| CN | 1762068 | 4/2006 | |
|---|---|---|---|
| CN | 101058677 | 10/2007 | |
| JP | 11327181 A | * 11/1999 | ............... G03G 5/07 |

OTHER PUBLICATIONS

Bowman, R. E.; Brunt, K. D.; Godfrey, K. E.; Kruszynska, L.; Reynolds, A. A.; Thrift, R. I.; Waite, D.; Williamson, W.R.N.; "Syntheses of flufenamic acid metabolites I and II and other N-arylanthranilic acids"; J. Chem. Soc., Perkin Transactions 1: Organic and Bio-Organic Chemistry (1972-1999) (1973), (1), 1-4.*
Authors: G. Goschloo et al.; "A Comparative Study of a Polyene-diphenylaniline Dye and Ru)dcbpy)$_2$(NCS)$_2$ in Electrolyte-based and Solid-State Dye-Sensitized Solar Cells;" Jan. 11, 2008; available online @ www.sciencedirect.com.
Authors: Gang Li et al.; "Efficient Structural Modification of Triphenylamine-Based Organic Dyes for Dye-Sensitized Solar Cells;" Jul. 9, 2008; J. Phys. Chem. C 2008, 112, 11591-11599.
Authors: Daniel P. Hagberg; "Molecular Engineering of Organic Sensitizers for Dye-Sensitizer Solar Cell Applications;" Apr. 18, 2008; J. Am. Chem. Soc. 2008, 6259-6266.

* cited by examiner

*Primary Examiner* — Johann R Richter
*Assistant Examiner* — Kofi Adzamli
(74) *Attorney, Agent, or Firm* — McKenna Long & Aldridge LLP

(57) ABSTRACT

Dyes for dye-sensitized solar cell are provided. Each of the dyes for a dye-sensitized solar cell according to an embodiment has a chemical structure:

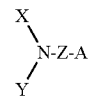

wherein each of X and Y may comprise a substituent, comprising aromatic hydrocarbon groups which are respectively independently substituted or unsubstituted, aromatic heterocyclic groups which are substituted or unsubstituted, and a combination thereof, Z may comprise aromatic hydrocarbon groups which are substituted or unsubstituted, heterocyclic groups which are substituted or unsubstituted, vinyl groups, and polyvinyl groups which are substituted or unsubstituted, and A may comprise acid functional groups.

7 Claims, 1 Drawing Sheet

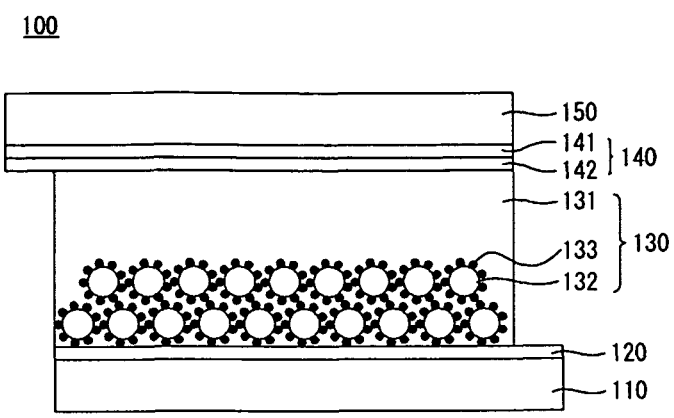

DYES FOR DYE SENSITIZED SOLAR CELL

This application claims the benefit of Korean Patent Application No. 10-2008-0117585 and No. 10-2008-0117601 each filed on Nov. 25, 2008 which are hereby incorporated by reference.

BACKGROUND OF THE INVENTION

1. Field of the Invention

This document relates to a solar cell, and more particularly, to dyes for a dye-sensitized solar cell.

2. Discussion of the Related Art

In order to solve the critical energy problem, a variety of researches for replacing the existing fossil fuels are recently being done. In particular, in order to replace petroleum resources that will become exhausted in several tens of years, a variety of researches for using natural energy, such as wind force, atomic energy, and solar power, are being done.

From among them, a solar cell is environmentally friendly because it is based on the unlimited resources, the sun, unlike other energy resources. The solar cell has recently been in the spotlight owing to the recent worldwide energy crisis since the development of a silicon (Si) solar cell in 1983.

In this silicon solar cell, however, there is a cutthroat competition among countries because of the supply and demand of Si raw materials, and the cost of production is high. In order to solve this problem, many local and overseas research institutions propose solutions. One of the solutions which can solve the critical energy crisis is a dye-sensitized solar cell. The dye-sensitized solar cell has been in the spotlight by the academic world since it was developed by a research team (lead by Dr. Micheal Graetzel) of the EPFL (Ecole Polytechnique Federale de Lausanne, in Switzerland) in 1991. Active researches have been done on the dye-sensitized solar cell in many research institutions.

The dye-sensitized solar cell is a photoelectrochemical solar cell, generally comprising photosensitive dye molecules capable of generating electron-hole pair by absorbing a visible ray and transition metal oxides capable of transferring the created electrons, unlike in the silicon solar cell. From among conventional dye-sensitized solar cells, a dye-sensitized solar cell using nano-particle titanium oxides has been chiefly researched and developed.

The dye-sensitized solar cell using nano-particle titanium oxides is advantageous in that it can be fabricated cheaply when compared with the existing silicon solar cell and can be applied to glass windows in the outer walls of a building or a glass greenhouse because of transparent electrodes, but is disadvantageous in that it has low photoelectric conversion efficiency. Accordingly, the dye-sensitized solar cell using nano-particle titanium oxides requires more researches.

The photoelectric conversion efficiency of a solar cell is proportional to the number of electrons generated by the absorption of sunlight. In order to increase the efficiency, the number of electrons generated and the amount of sunlight absorbed need to be increased by increasing the amount of dyes adsorbed by titanium oxide nano-particles, and generated excited electrons needs to be prevented from being extinguished through electron-hole recombination.

There are several methods, for example, a method of fabricating the particles of oxide semiconductors having a nanometer size in order to increase the amount of dyes absorbed per unit area, a method of increasing the reflectance of a platinum electrode in order to increase the amount of sunlight absorbed, and a method of mixing semiconductor oxide light scattering agents of a several micrometer size.

However, the conventional methods have reached the limit on improving the photoelectric conversion efficiency of a solar cell. Accordingly, there is an urgent need for the development of a new technology for improving the efficiency.

SUMMARY OF THE INVENTION

An aspect of this document is to provide dyes for a dye-sensitized solar cell with excellent photoelectric conversion efficiency and an excellent lifespan characteristic and a solar cell including the same.

Each of dyes for a dye-sensitized solar cell according to an embodiment of this document may have the following chemical structure 1.

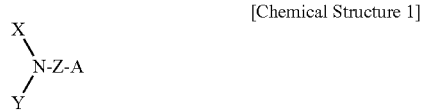

[Chemical Structure 1]

In the above structure, each of X and Y may comprise a substituent, comprising aromatic hydrocarbon groups which are respectively independently substituted or unsubstituted, aromatic heterocyclic groups which are substituted or unsubstituted, and a combination thereof, Z may comprise aromatic hydrocarbon groups which are substituted or unsubstituted, heterocyclic groups which are substituted or unsubstituted, vinyl groups, and polyvinyl groups which are substituted or unsubstituted, and A may comprise acid functional groups.

BRIEF DESCRIPTION OF THE DRAWINGS

The implementation of this document will be described in detail with reference to the following drawing in which like numerals refer to like elements.

FIG. 1 is a diagram showing a dye-sensitized solar cell according to an embodiment of this document.

DETAILED DESCRIPTION OF THE EMBODIMENTS

Hereinafter, implementations of this document will be described in detail with reference to the attached drawing.

Each of dyes for a dye-sensitized solar cell according to an embodiment of this document may have the following chemical structure 1.

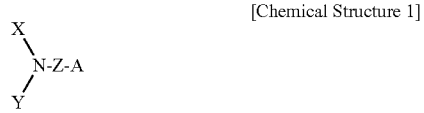

[Chemical Structure 1]

In the above structure, each of X and Y may comprise a substituent, comprising aromatic hydrocarbon groups which are respectively independently substituted or unsubstituted, aromatic heterocyclic groups which are substituted or unsubstituted, and a combination thereof, Z may comprise aromatic hydrocarbon groups which are substituted or unsubstituted, heterocyclic groups which are substituted or unsubstituted, vinyl groups, and polyvinyl groups which are substituted or unsubstituted, and A may comprise acid functional groups.

At least one of the X and Y may comprise fluoric groups.

Each of the X and Y may comprise a substituent, comprising aromatic hydrocarbon groups which are configured to have the number of carbons of 5 to 20 and are independently substituted or unsubstituted, aromatic heterocyclic groups which are substituted or unsubstituted, and a combination thereof. Here, at least one of the X and Y may comprise fluoric groups.

Each of the X and Y may comprise a substituent selected from the group consisting of alkyl, alkoxy, aryl groups, arylene groups, alkylene groups, and a combination thereof.

The Z may comprise a substituent selected from the group consisting of thiophene, vinyl groups, polyvinyl groups, benzene, naphthalene, antracence, fluorene, biphenyl, pyran, pyrrole, carbazole, and a combination thereof.

The Z may comprise a substituent selected from the group consisting of alkyl, alkoxy, aryl groups, alkenyl groups, arylene groups, alkylene groups, and a combination thereof.

The A may comprise a substituent selected from the group consisting of carboxy acid groups, phosphorous acid groups, sulfon acid groups, phosphinic acid groups, hydroxy acid groups, oxycarboxy acids, acid amide, and a combination thereof.

The X—N—Y may comprise any one of the following compounds.

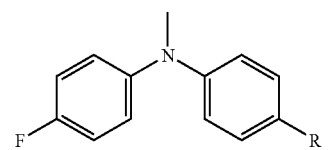

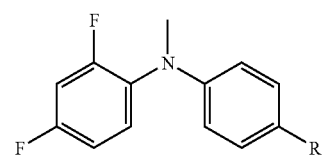

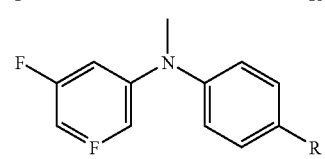

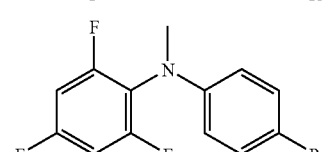

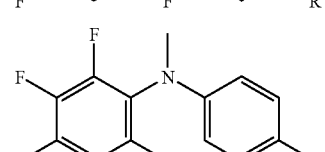

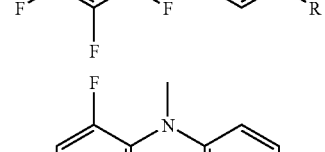

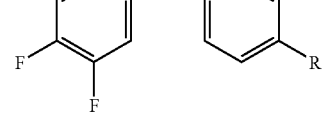

-continued

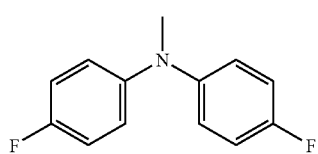

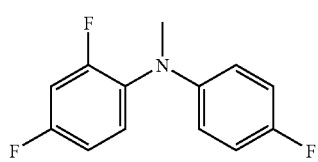

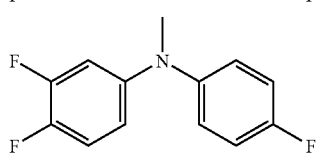

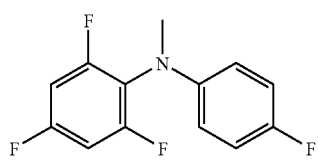

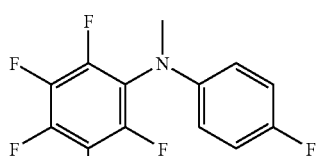

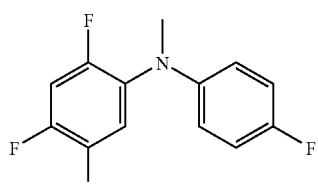

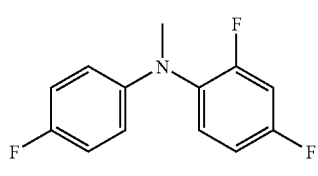

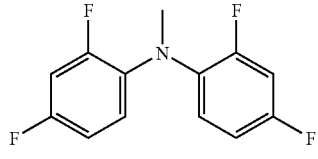

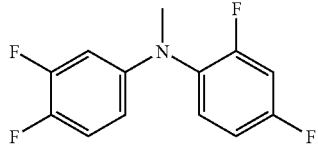

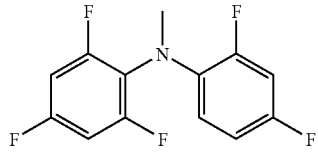

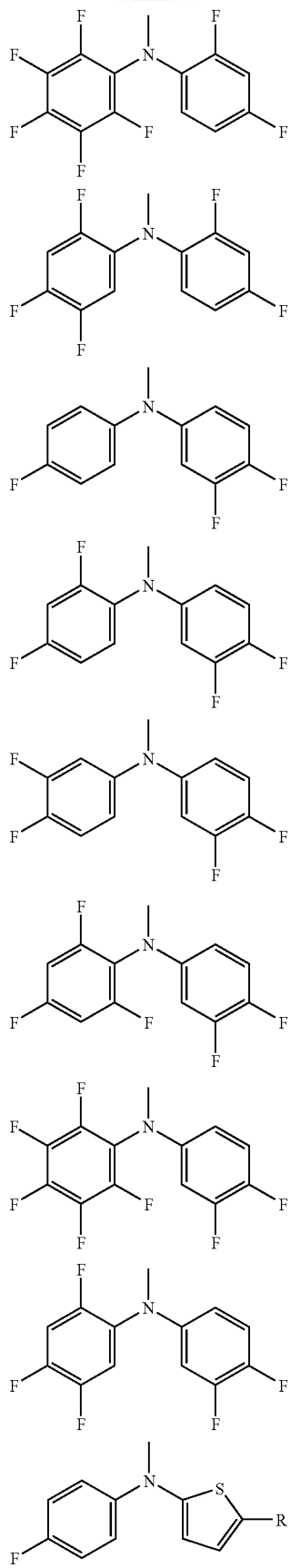
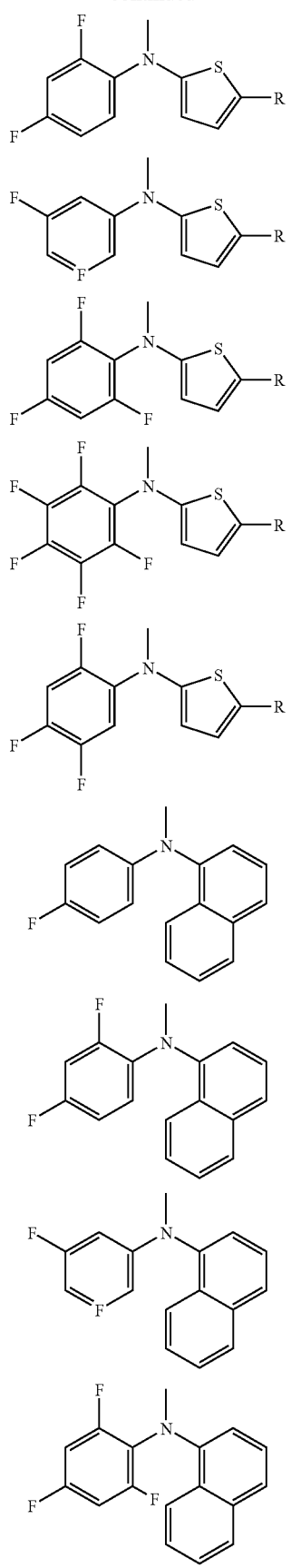

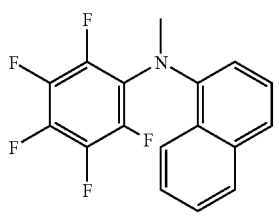
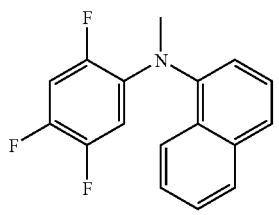
where R may comprise alkyl groups or trimethylsilyl groups, that is, H or C1 to C8,
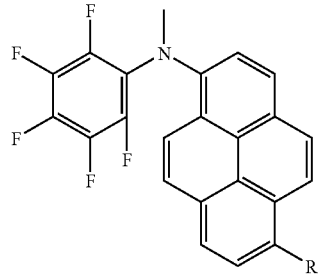
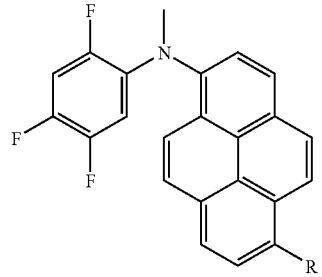
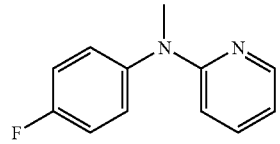
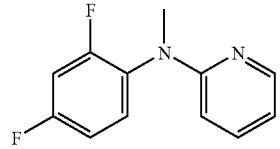
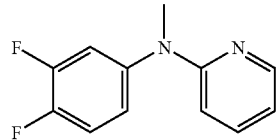
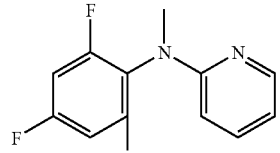
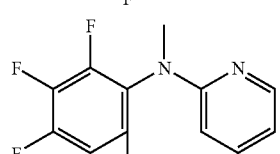
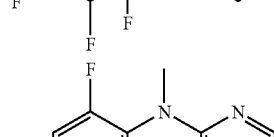
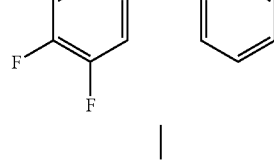

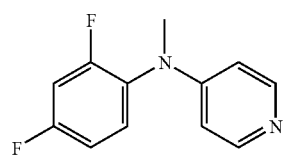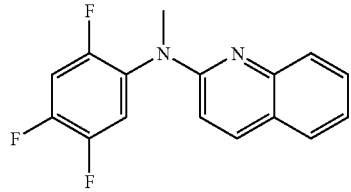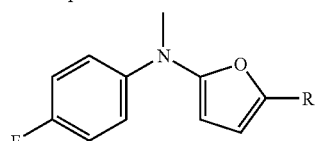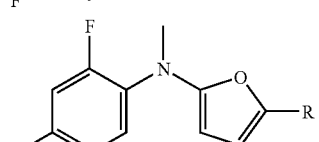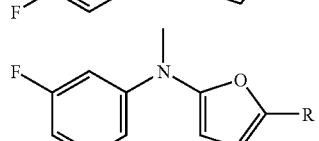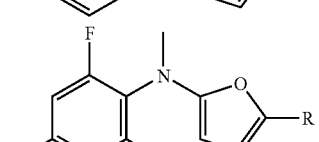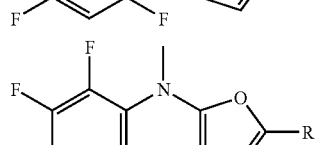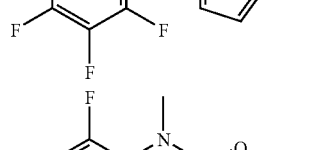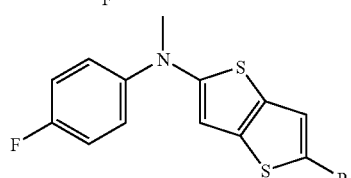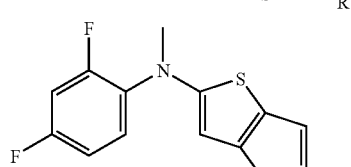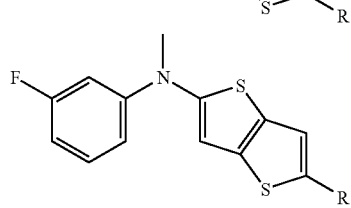

-continued
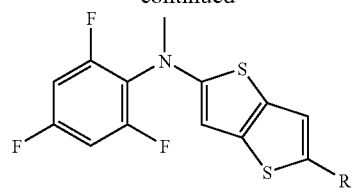
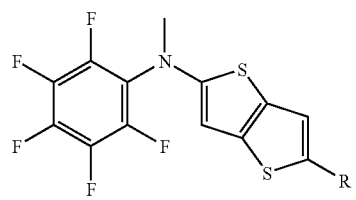
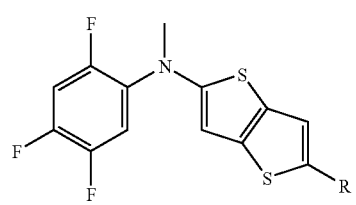
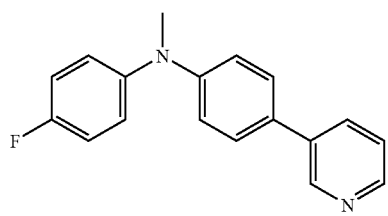
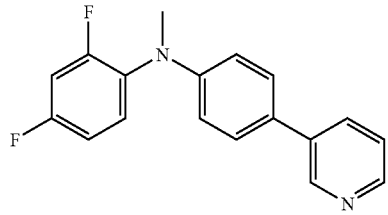
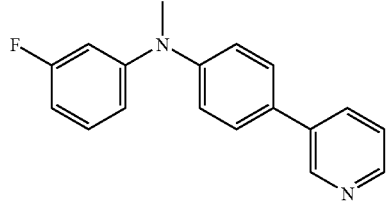
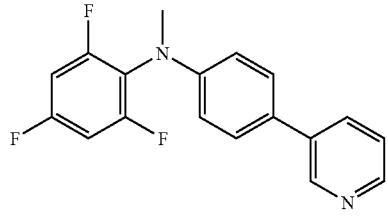
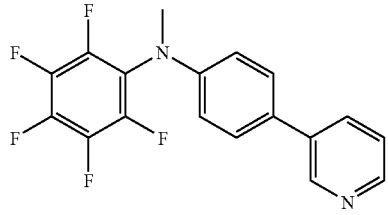
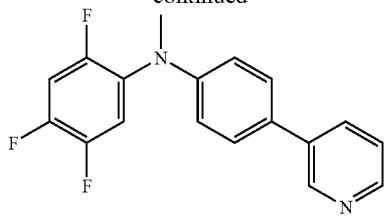
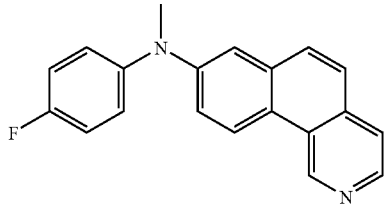
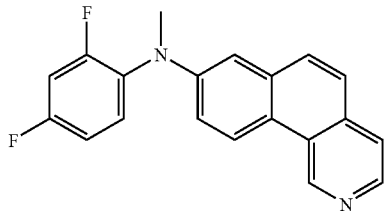
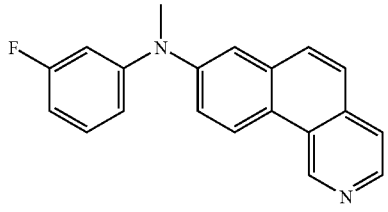
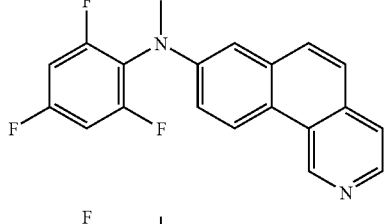
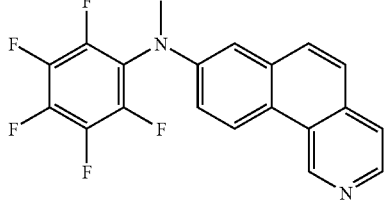
where R may comprise alkyl groups or trimethylsilyl groups, that is, H, F or C1 to C8, and
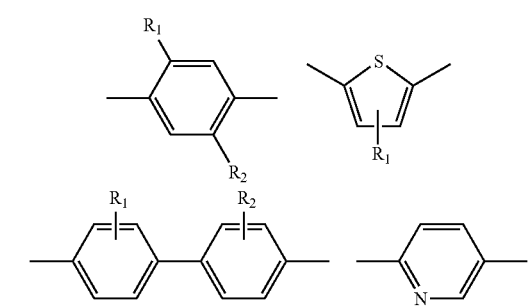

-continued

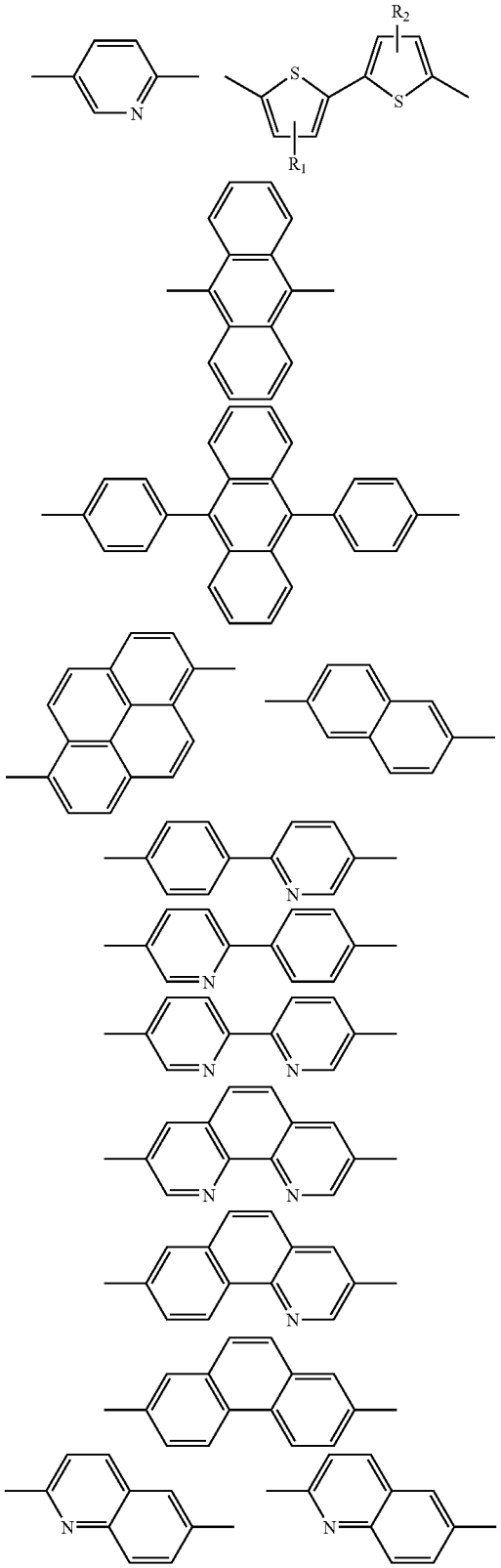

where $R_1$ and $R_2$ may comprise alkyl groups, alkoxy groups, and alkenyl groups, that is, H or C1 to C8.

A dye-sensitized solar cell according to an embodiment of the present invention may comprise the above-described dye.

At least one of the X and Y may comprise silane derivatives substituted with alkyl groups or aryl groups.

Each of the X and Y may comprise a substituent, comprising aromatic hydrocarbon groups which are configured to have the number of carbons of 5 to 20 and are independently substituted or unsubstituted, aromatic heterocyclic groups which are substituted or unsubstituted, and a combination thereof. In this case, at least one of the X and Y may comprise silane derivatives substituted with alkyl groups, alkoxy groups, aryl groups, alkenyl groups, arylene groups, and alkylene groups.

Each of the X and Y may comprise a substituent selected from the group consisting of alkyl, alkoxy, aryl groups, arylene groups, alkylene groups, and a combination thereof.

The Z may comprise a substituent selected from the group consisting of thiophene, vinyl groups, polyvinyl groups, benzene, naphthalene, antracence, fluorene, biphenyl, pyran, pyrrole, carbazole, and a combination thereof.

The Z may comprise a substituent selected from the group consisting of alkyl, alkoxy, aryl groups, alkenyl groups, arylene groups, alkylene groups, and a combination thereof.

The A may comprise a substituent selected from the group consisting of carboxy acid groups, phosphorous acid groups, sulfon acid groups, phosphinic acid groups, hydroxy acid groups, oxycarboxy acids, and a combination thereof.

The X—N—Y may comprise any one of the following compounds.

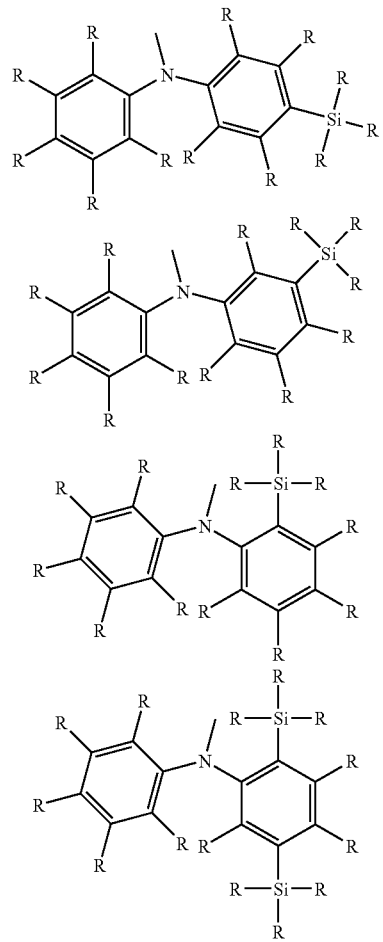

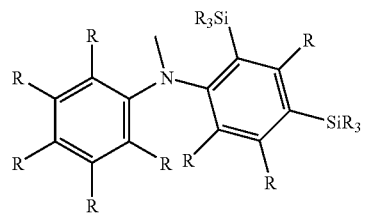
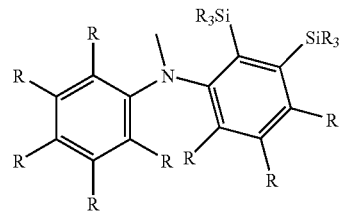
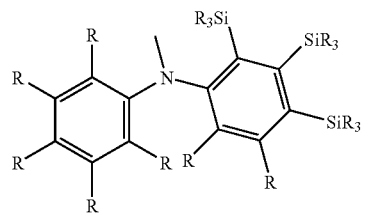
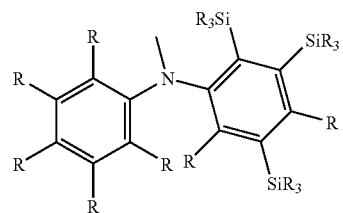
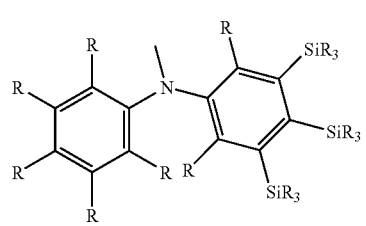
where R may comprise alkyl groups, alkoxy groups, aryl groups, alkenyl groups, arylene groups, or alkylene groups, which are respectively independently H or C1 to C8,
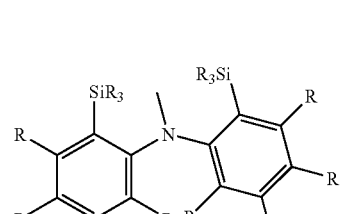
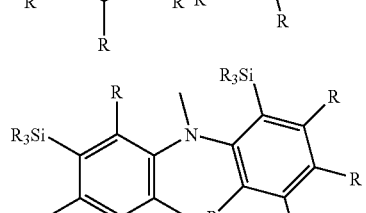
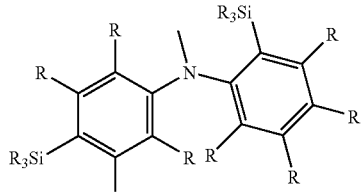
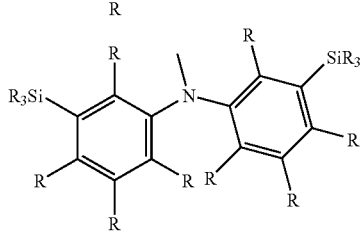
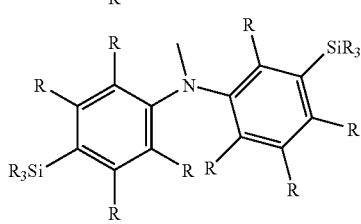
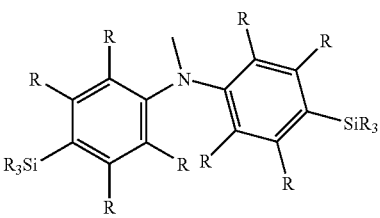
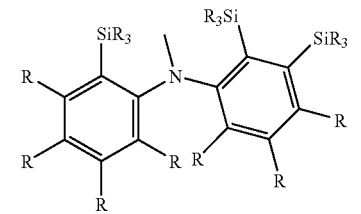
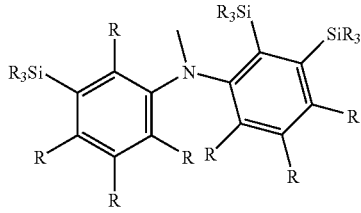
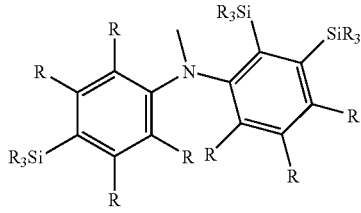
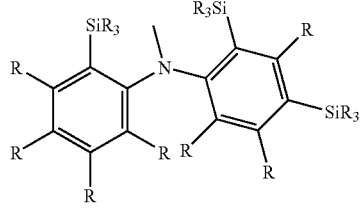

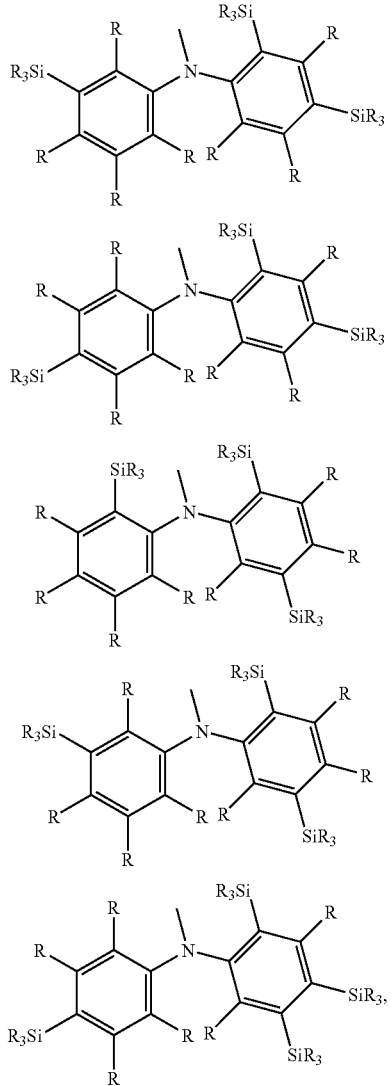
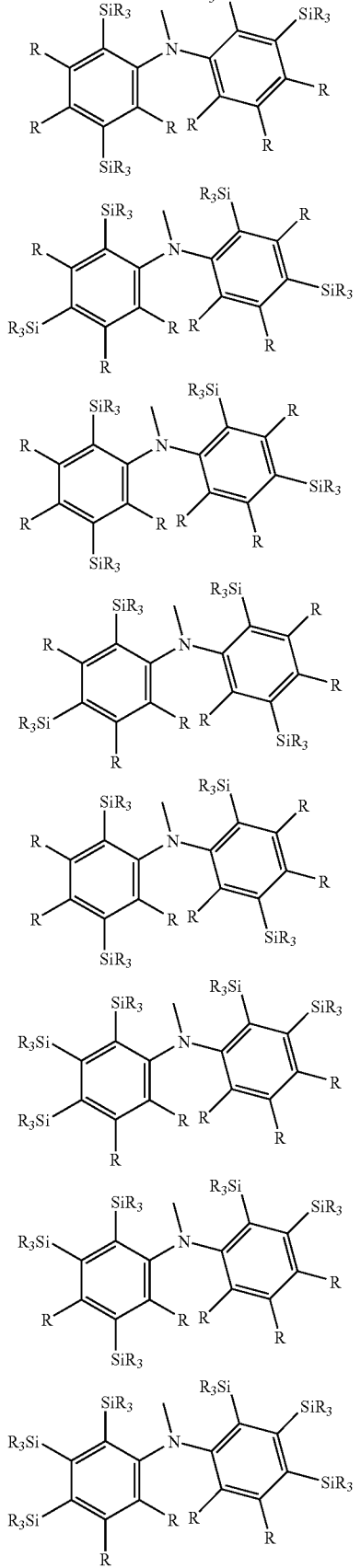
where R may comprise alkyl groups, alkoxy groups, aryl groups, alkenyl groups, arylene groups, or alkylene groups which are respectively independently H or C1 to C8,

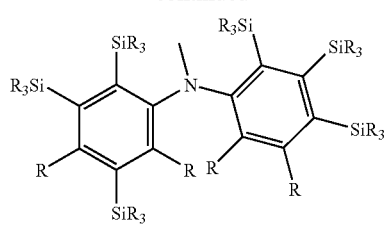
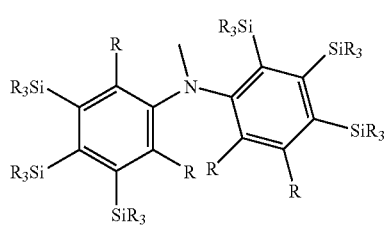
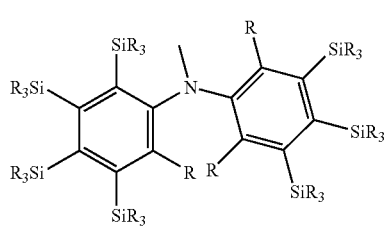
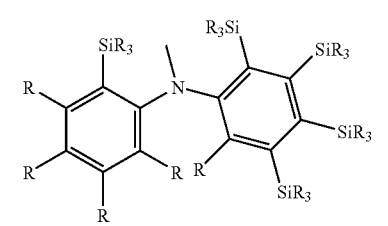
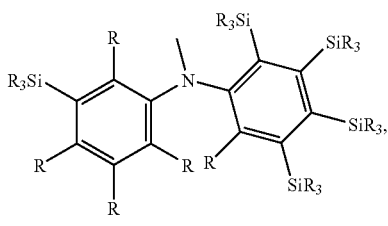
where R may comprise alkyl groups, alkoxy groups, aryl groups, alkenyl groups, arylene groups, or alkylene groups which are respectively independently H or C1 to C8,
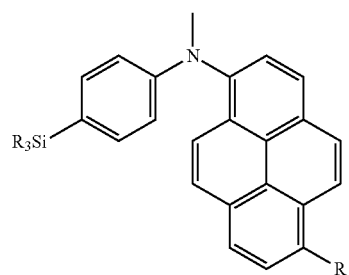
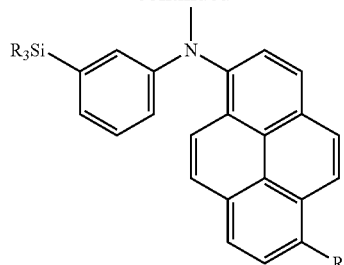
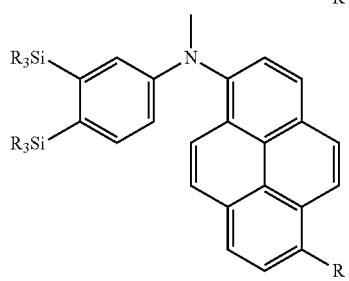
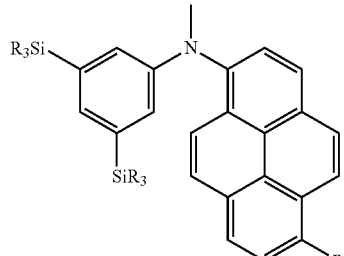
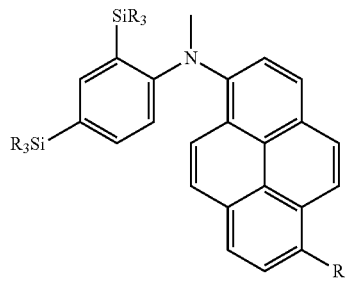
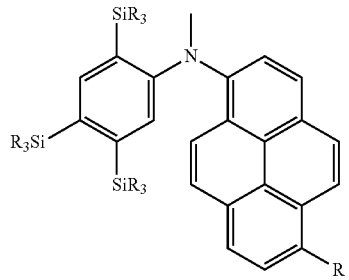
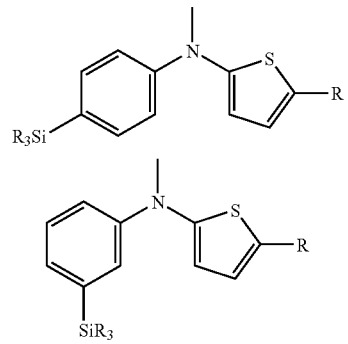

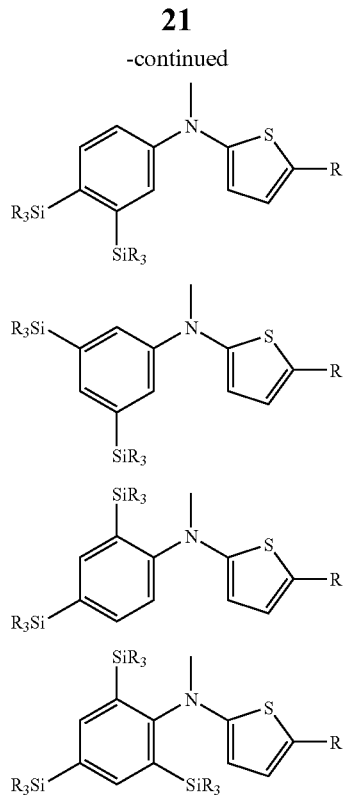

where R may comprise alkyl groups, alkoxy groups, aryl groups, alkenyl groups, arylene groups, or alkylene groups which are respectively independently H or C1 to C8, and

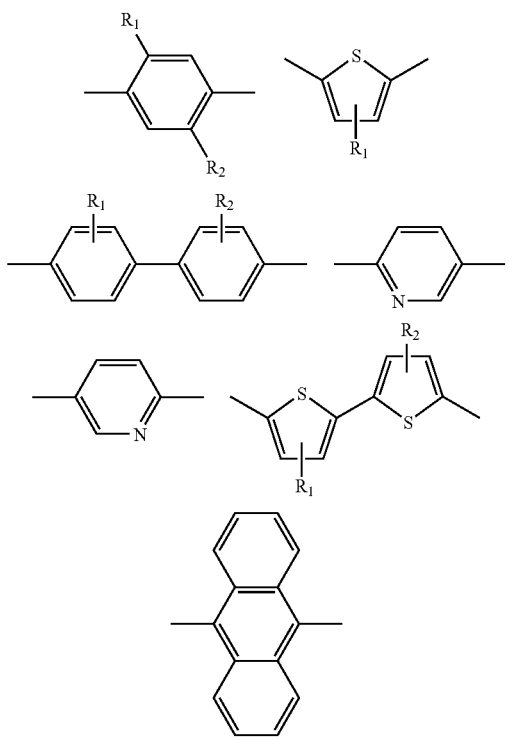

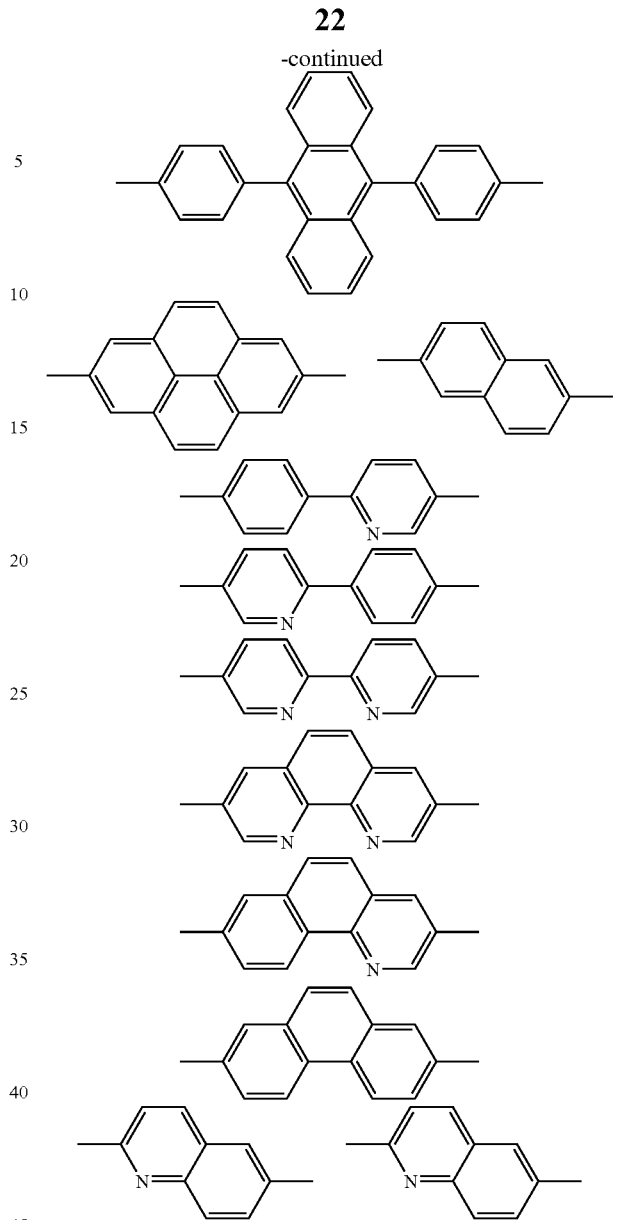

where each of $R_1$ and $R_2$ may comprise alkyl groups, alkoxy groups, aryl groups, alkenyl groups, arylene groups, or alkylene groups which are H or C1 to C8.

A dye-sensitized solar cell according to an embodiment of this document may comprise the above-described dye.

Hereinafter, embodiments of this document are described with reference to the accompanying drawing.

FIG. 1 is a diagram showing a dye-sensitized solar cell according to an embodiment of this document.

Referring to FIG. 1, the dye-sensitized solar cell 100 has a sandwitch structure in which a first electrode 120 and a second electrode 140 are coalesced with each other in a sheet form. More particularly, the dye-sensitized solar cell 100 may have a structure in which the first electrode 120 is placed over a first substrate 110, and the second electrode 140 is opposite to the first electrode 120 over a second substrate 150 opposite to the first electrode 120.

A light adsorption layer 130 may be placed between the first electrode 120 and the second electrode 140. The light adsorption layer 130 may comprise an electrolyte 131, semiconductor quantum dots 132, and dyes 133 adsorbed to the semiconductor quantum dots 132.

The first substrate 110 may be made of glass or plastic, but are not specifically limited to any materials as long as they have transparency in order for external light to be incident thereon. In this case, plastic may comprise, for example, polyethyleneterephthalate (PET), polyethylenenaphthalate (PEN), polycarbonate (PC), polypropylene (PP), polyimide (PI), triacetyl cellulose (TAC) or a copolymer of them.

The first substrate 110 may be doped with any material selected from the group consisting of titanium, indium, gallium, and aluminum.

The first electrode 120 may comprise a conductive metal oxide layer.

The conductive metal oxide layer may be selected from the group consisting of indium tin oxide (ITO), fluorine tin oxide (FTO), ZnO—($Ga_2O_3$ or $Al_2O_3$), tin oxide, antimony tin oxide (ATO), zinc oxide (ZnO), and a mixture thereof. $F:SnO_2$ may be chiefly used as the conductive metal oxide layer.

The light adsorption layer 130 may comprise the electrolyte 131, the semiconductor quantum dots 132, and the dyes 133.

A redox electrolyte may be used as the electrolyte 131. More particularly, the redox electrolyte may comprise halogen oxidation-reduction system electrolytes comprising halogen oxidation-reduction system electrolytes comprising halogen compounds and halogen molecules having halogen ions as large ions, metallic oxidation-reduction system electrolytes such as ferrocyanide-ferrocyanide or ferrocene-ferricenium ions and a metallic complex such as a cobalt complex, and organic oxidation-reduction system electrolytes such as alkylthiol-alkyldisulfide, viologen dyes, and hydroquinone-quinone. The halogen oxidation-reduction system electrolytes may be preferably used as the electrolyte 131.

Halogen molecules in the halogen oxidation-reduction system electrolytes comprising the halogen compounds-halogen molecules may chiefly include iodine molecules. Further, the halogen compounds having the halogen ions as large ions may comprise halide metallic salts such as LiI, NaI, $CaI_2$, $MgI_2$, and CuI, organic ammonium salts of halogen such as tetraalkylammonium iodine, imidazoliumiodine, and pyridiniumiodine, or $I_2$.

In the case where the redox electrolyte is comprised in the form of a solution comprising the redox electrolyte, the redox electrolyte may have a solvent which is inert in terms of the cell chemistry property. The solvent of the redox electrolyte may comprise, for example, acetonitrile, propylenecarbonate, ethylenecarbonate, 3-methoxypropionitrile, methoxyacetonitrile, ethylene glycol, propyleneglycol, diethylene glycol, triethylene glycol, butyrolactone, dimethoxyethane, dimethylcarbonate, 1,3-dioxolane, methylformate, 2-methyltetrahydrofuran, 3-methoxy-oxazolidine-2-on, sulfolane, tetrahydrofuran, and water. In particular, acetonitrile, propylenecarbonate, ethylenecarbonate, 3-methoxypropionitrile, ethylene glycol, 3-methoxy-oxazolidine-2-on, and butyrolactone may be chiefly used as the solvent. The above solvents may be used either alone or in combination thereof.

Not only a simple semiconductor represented by silicon, but also a compound semiconductor or a compound having a perovskite structure may be used as the semiconductor quantum dots 132.

The semiconductor may comprise an n type semiconductor in which electrons in the conduction band become carriers in an excitation state and thus provide anode current. Metallic oxide selected from the group consisting of titanium, tin, zinc, tungsten, zirconium, gallium, indium, yttrium, niobium, tantalum, and vanadium may be used as the compound semiconductor. Titanium oxide, tin oxide, zinc oxide, niobium oxide, titanium oxide, strontium, or a mixture thereof may be chiefly used as the compound semiconductor. The titanium oxide of an anatase type may be chiefly used as the compound semiconductor. The types of the semiconductor are not limited, but may be used either alone or a combination thereof.

Each of the semiconductor quantum dots 132 may have a mean diameter of 1 to 500 nm, more particularly, 1 to 100 nm. In addition, some of the semiconductor quantum dots 132 may have a large diameter and the remaining thereof may have a small diameter. Alternatively, the semiconductor quantum dots 132 may be configured to have a multi-layer.

The semiconductor quantum dots 132 may be formed using a method of directly forming semiconductor quantum dots on a substrate through spray in the form of a thin film, a method of electrically depositing a thin film of semiconductor quantum dots using a substrate as an electrode, or a method of coating a paste, including quantum dots that can be obtained by hydrolyzing a slurry of semiconductor quantum dots or a precursor of semiconductor quantum dots, on a substrate, and then performing dry, curing or sintering on the paste.

The dyes 133 for generating excited electrons by absorbing external light may be adsorbed on the surface of each of the semiconductor quantum dots 132.

The light adsorption layer 130 may have a thickness of 15 μm or less, more particularly, 1 to 15 μm.

The second electrode 140 may be placed over the light adsorption layer 130. The second electrode 140 may comprise a transparent electrode 141 and a catalyst electrode 142.

The transparent electrode 141 may be comprised of transparent material such as indium tin oxide, fluoro tin oxide, antimony tin oxide, zinc oxide, tin oxide, or ZnO—($Ga_2O_3$ or $Al_2O_3$).

The catalyst electrode 142 functions to activate the redox couple. Platinum, gold, ruthenium, palladium, rhodium, iridium, osmium, carbon, titanium oxide, or conductive material such as conductive polymer may be used as the catalyst electrode 142.

Further, in order to improve the catalyst effect of oxidation-reduction, the catalyst electrode 142 being opposite to the first electrode 120 may have a micro structure, thereby increasing the surface area. For example, lead or gold may have a black state, and carbon may have a porous state. In particular, a black state of platinum may be formed using an anodic oxidation method of platinum or a chloroplatinic acid processing, and a porous state of carbon may be formed using a method such as sintering of carbon quantum dots or curing of oraganic polymer.

The second substrate 150 may be made of glass or plastic as in the first substrate 110. The plastic may comprise, for example, polyethylene terephthalate, polyethylenethalate, polycarbonate, polypropylene, polyimide, and triacetylcellulose.

If sunlight is incident on the dye-sensitized solar cell 100 having the above construction, light quanta are first absorbed by the dyes 133 within the light adsorption layer 130. Accordingly, the electrons of the dyes 133 shift from the ground state to the excited state, thus creating electron-hole pairs. The electrons of the excited state are injected into the conduction band on the interface of each of the semiconductor quantum dots 132. The injected electrons are transferred to the first electrode 120 via the interface and are then moved to the second electrode 140 (that is, a counter electrode) via an external circuit.

Meanwhile, the dyes 133 oxidized as a result of the shift of the electrons are reduced by the ions of an oxidation-reduction couple within the electrolyte 131. A reduction reaction is generated between the oxidized ions and the electrons that have reached the interface of the second electrode 140 in order to form charge neutrality. Consequently, the dye-sensitized solar cell 100 is operated.

The dyes 133 used in the dye-sensitized solar cell 100 according to an embodiment of this document are described below in detail.

Each of the dyes for the dye-sensitized solar cell according to an embodiment of this document may have the following chemical structure 1.

[Chemical Structure 1]

In the above structure, each of X and Y may comprise a substituent, comprised of aromatic hydrocarbon groups which are respectively independently substituted or unsubstituted, aromatic heterocyclic groups which are substituted or unsubstituted, and a combination thereof, Z may comprise aromatic hydrocarbon groups which are substituted or unsubstituted, heterocyclic groups which are substituted or unsubstituted, vinyl groups, and polyvinyl groups which are substituted or unsubstituted, and A may comprise acid functional groups.

Furthermore, each of the X and Y may comprise a substituent, comprised of aromatic hydrocarbon groups which are configured to have the number of carbons of 5 to 20 and are independently substituted or unsubstituted, aromatic heterocyclic groups which are substituted or unsubstituted, and a combination thereof. In this case, at least one of the X and Y may comprise fluoric groups.

The heterocyclic groups may be selected from among substituents comprising pyran, pyrrole, thiophene, carbazole, and a combination thereof.

Each of the X and Y may comprise a substituent selected from the group consisting of thiophene, vinyl groups, polyvinyl groups, benzene, naphthalene, antrancence, fluorene, biphenyl, pyran, pyrrole, carbazole, and a combination thereof.

The Z may comprise a substituent selected from the group consisting of thiophene, vinyl groups, polyvinyl groups, benzene, naphthalene, antrancence, fluorene, biphenyl, pyran, pyrrole, carbazole, and a combination thereof.

The Z may comprise a substituent selected from the group consisting of alkyl, alkoxy, aryl groups, alkenyl groups, arylene groups, alkylene groups, and a combination thereof.

In this case, each of the alkyl groups may comprise an alkyl group which is configured to have the number of carbons of 1 to 20 and has been substituted or unsubstituted. Each of the alkoxy groups may be configured to have the number of carbons of 1 to 20 and may have experienced oxygen-containing substitution or non-substitution. The aryl groups may be used either alone or in combination thereof. Each of the aryl group may be a carbocycle aromatic compound such as phenyl, naphthyl, tetrahydronaphthyl, or biphenyl. The carbocycle aromatic compound may be configured to have the number of carbons of 6 to 30 and have one or more rings. Each of the alkylene groups may have a radical shape in which both ends of an alkyl group can be combined with each other. Here, the alkyl group is the same as that described above.

The A may comprise a substituent selected from the group consisting of carboxy acid groups, phosphorous acid groups, sulfon acid groups, phosphinic acid groups, hydroxy acid groups, oxycarboxy acids, acid amide, and a combination thereof.

The X—N—Y may comprise any one of the following compounds.

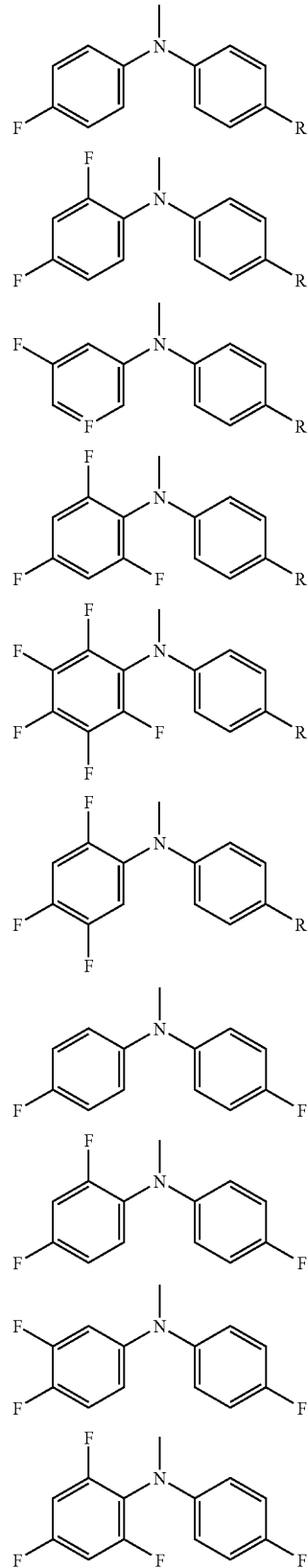

-continued

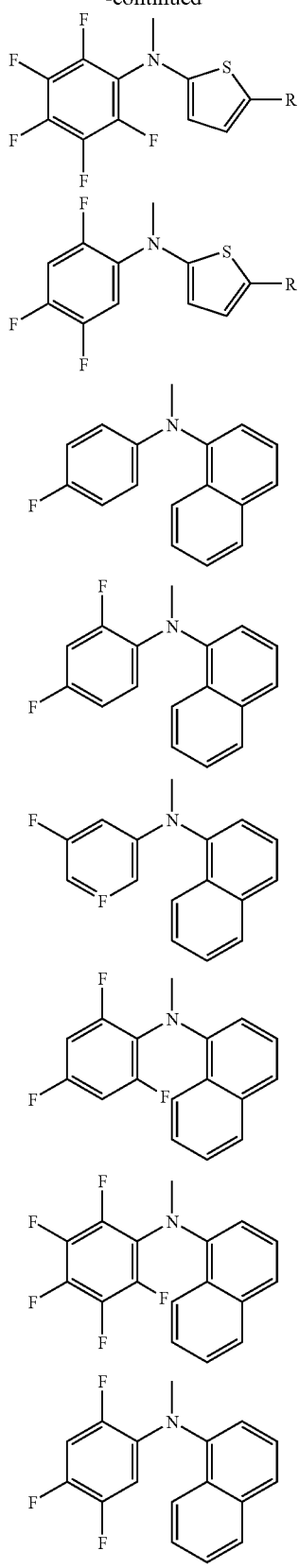
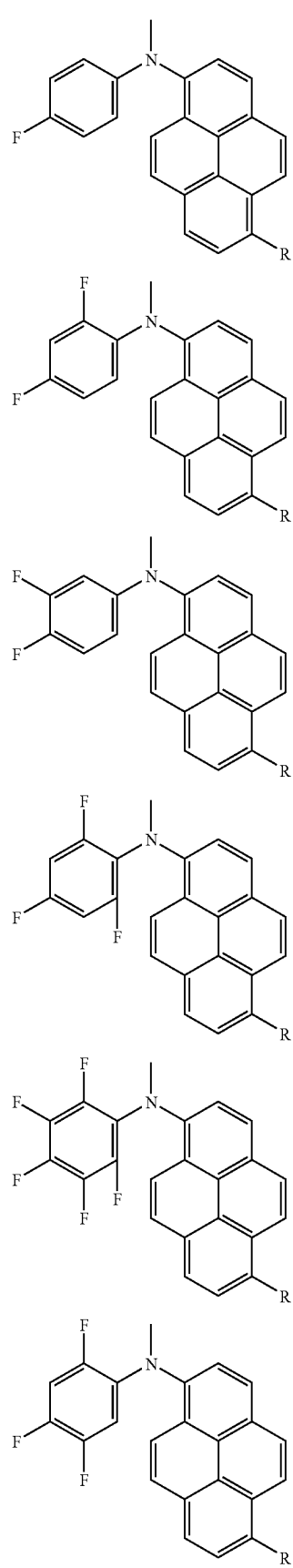
where R may comprise alkyl groups or trimethylsilyl groups, that is, H or C1 to C8, -continued
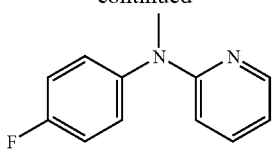
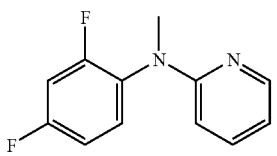
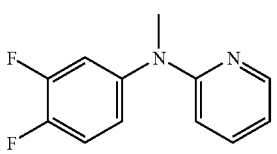
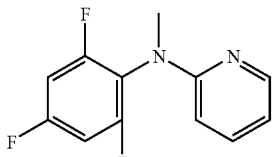
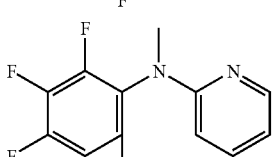
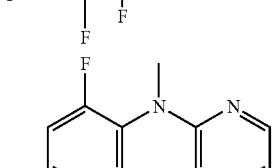
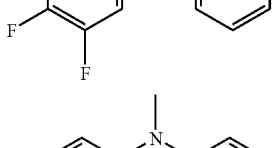
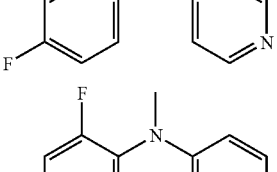
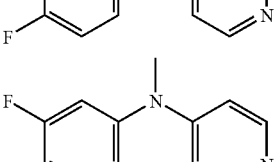
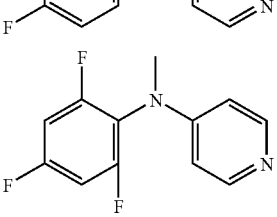
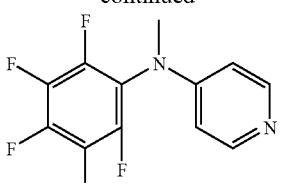
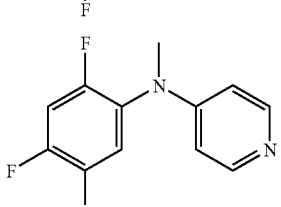
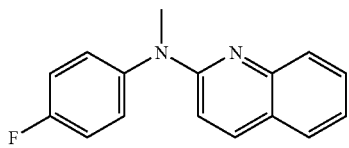
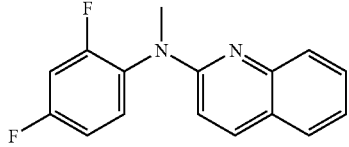
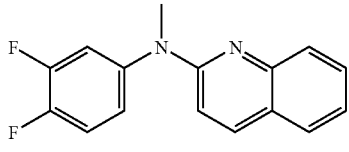
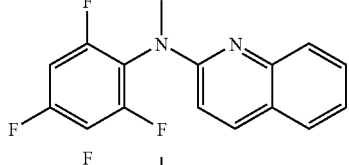
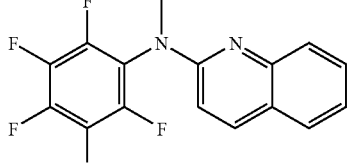
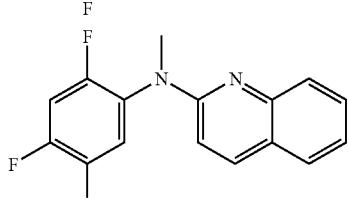
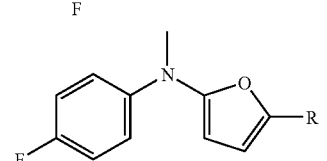
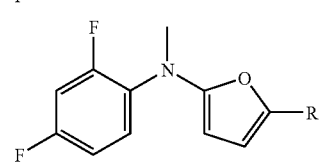

-continued
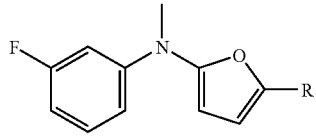
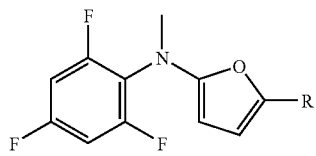
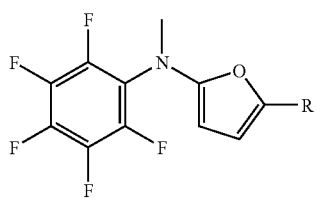
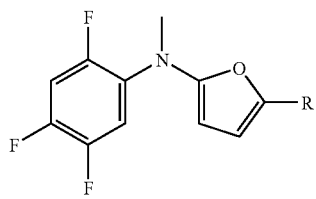
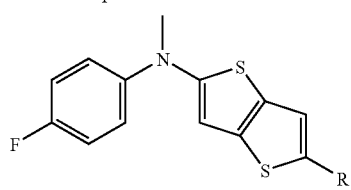
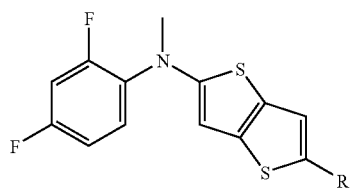
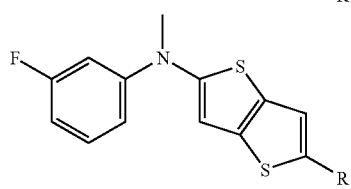
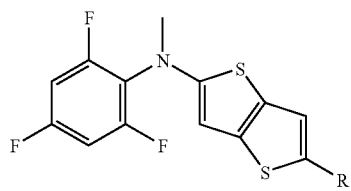
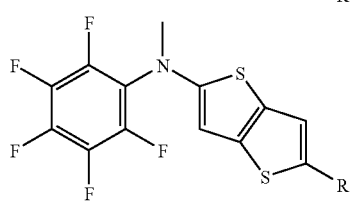
-continued
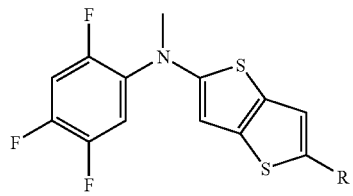
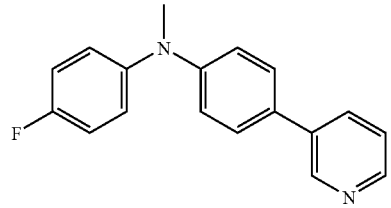
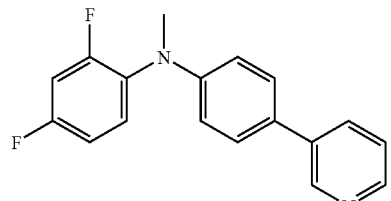
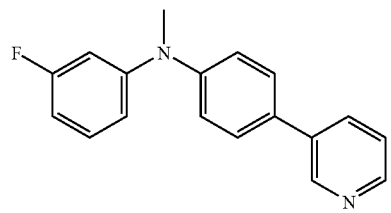
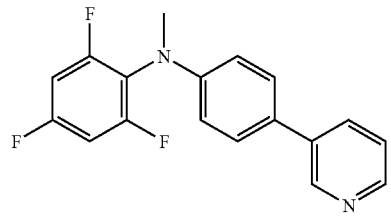
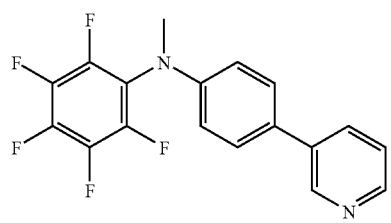
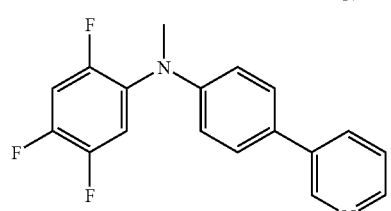
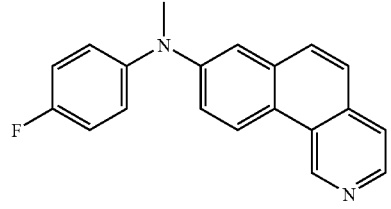

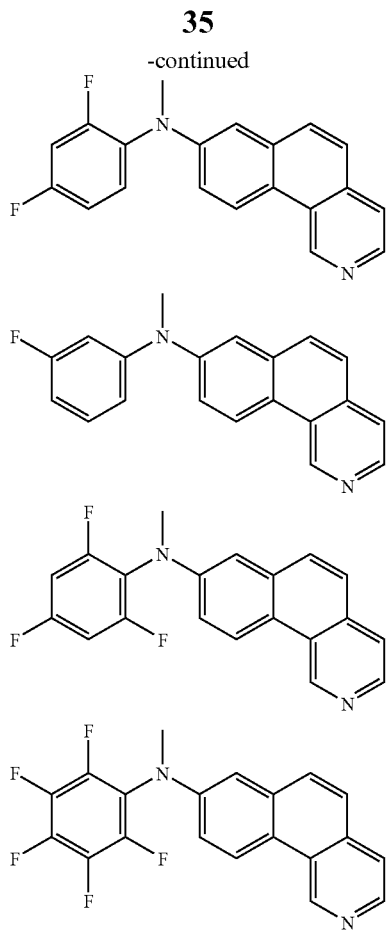

where R may comprise alkyl groups or trimethylsilyl groups, that is, H, F or C1 to C8, and

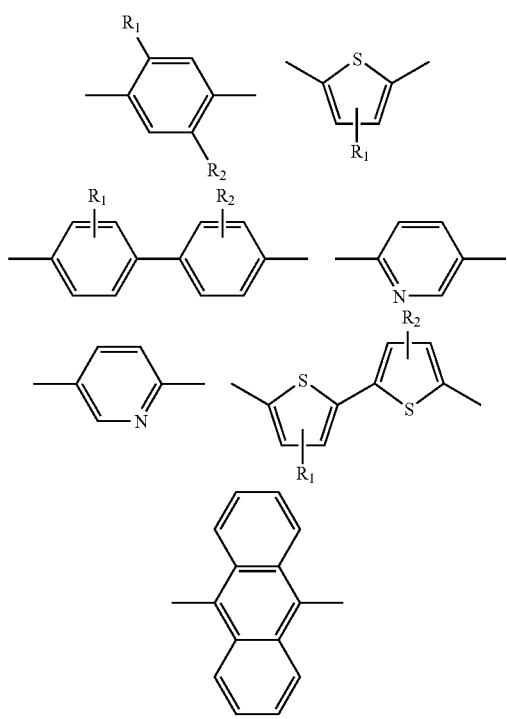

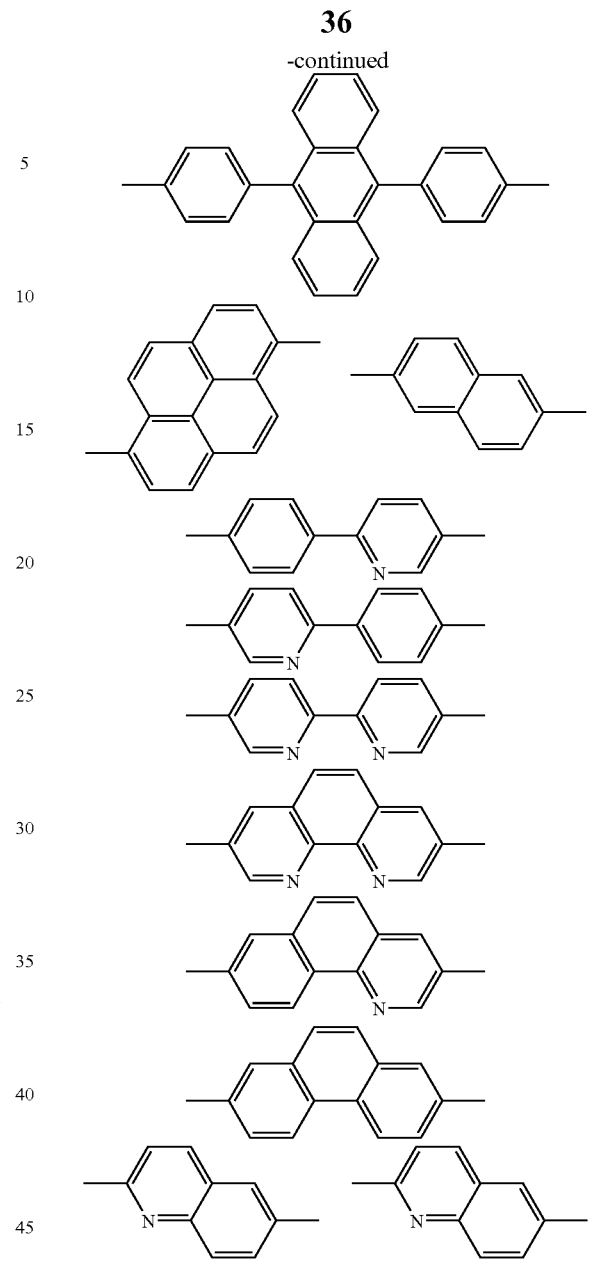

where $R_1$ and $R_2$ may comprise alkyl groups, alkoxy groups, and alkenyl groups, that is, H or C1 to C8. Meanwhile, the dyes 133 used in the dye-sensitized solar cell 100 according to another embodiment of this document are described below in detail.

Each of the dyes for dye-sensitized solar cell according to another embodiment of this document may have the following chemical structure 1.

[Chemical Structure 1]

In the above structure, each of the X and Y may be a substituent, comprising aromatic hydrocarbon groups which are respectively independently substituted or unsubstituted, aromatic heterocyclic groups which are substituted or unsubstituted, and a combination thereof.

In this case, each of the aromatic hydrocarbon groups may comprise a substituent, comprising benzene, naphthalene, antracence, fluorene, biphenyl, and a combination thereof. The heterocyclic groups may be selected from among substituents, comprising pyran, pyrrole, thiophene, carbazole, and a combination thereof.

Further, at least one of the X and Y may comprise silane derivatives substituted with alkyl groups or aryl groups. Each of the X and Y may be a substituent, comprising aromatic hydrocarbon groups which are configured to have the number of carbons 5 to 20 and are respectively independently substituted or unsubstituted, aromatic heterocyclic groups which are substituted or unsubstituted, and a combination thereof. In this case, at least one of the X and Y may comprise silane derivatives substituted with alkyl groups, alkoxy groups, aryl groups, alkenyl groups, arylene groups, or alkylene groups.

Further, each of the X and Y may comprise a substituent selected from the group consisting of alkyl groups, alkoxy groups, aryl groups, arylene groups, alkylene groups, and a combination thereof. Each of the alkyl groups may be selected from among substituents, comprising alkyl groups which are respectively configured to have the number of carbons 1 to 20 and have been substituted or unsubstituted. Each of the alkoxy groups may be selected from among substituents, comprising alkoxy groups containing oxygen and having alkyl groups which are respectively configured to have the number of carbons of 1 to 20 and have been substitution or unsubstituted. The aryl groups may be used either alone or in combination thereof. The aryl groups may be carbocycle aromatic compounds such as phenyl, naphthyl, tetrahydronaphthyl, indane, or biphenyl. Each of the aryl groups may have the number of carbons of 6 to 30 and comprise one or more rings. Each of the alkylene groups may have a radical shape in which both ends of an alkyl group can be combined with each other. Here, the alkyl group is the same as that described above.

The Z may comprise aromatic hydrocarbon groups which are substituted or unsubstituted, heterocyclic groups which are substituted or unsubstituted, vinyl groups, or polyvinyl groups which are substituted or unsubstituted. More particularly, the Z may comprise a substituent selected from the group consisting of thiophene, vinyl groups, polyvinyl groups, benzene, naphthalene, antracence, fluorene, biphenyl, pyran, pyrrole, carbazole, and a combination thereof. Further, the Z may comprise a substituent selected from the group consisting of alkoxy, aryl groups, alkenyl groups, arylene groups, alkylene groups, and a combination thereof.

The A may comprise acid functional groups or comprise a substituent selected from the group consisting of carboxy acid groups, phosphorous acid groups, sulfon acid groups, phosphinic acid groups, hydroxy acid groups, oxycarboxy acids, and a combination thereof.

Furthermore, the X—N—Y may comprise any one of the following compounds.

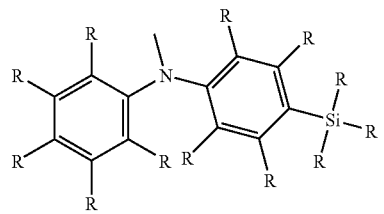

-continued

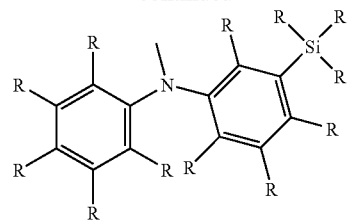

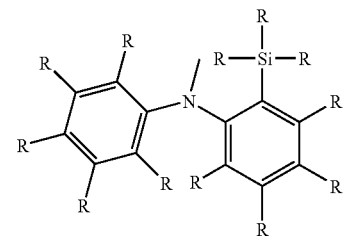

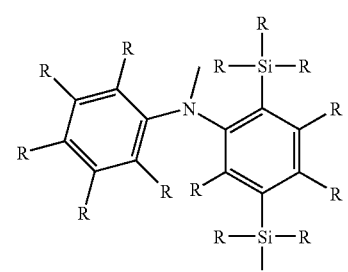

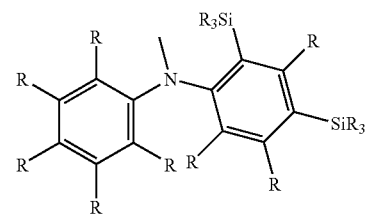

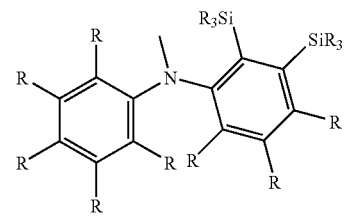

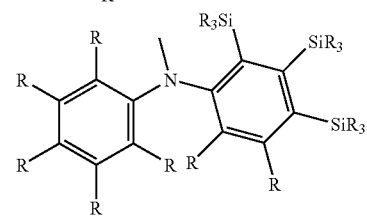

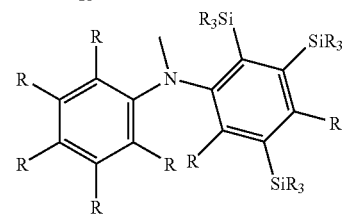

-continued
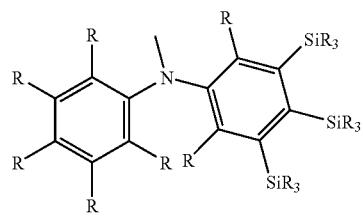
where R may comprise alkyl groups, alkoxy groups, aryl groups, alkenyl groups, arylene groups, or alkylene groups which are respectively independently H or C1 to C8,
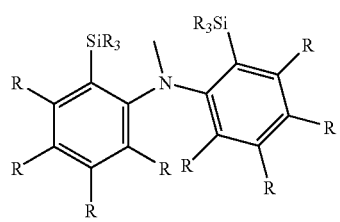
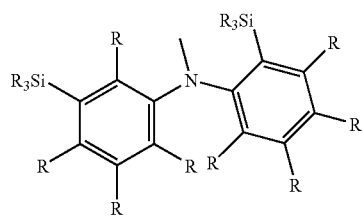
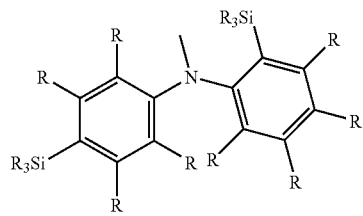
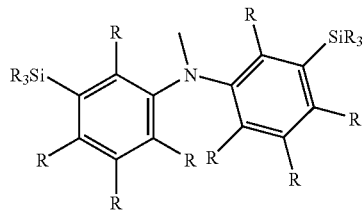
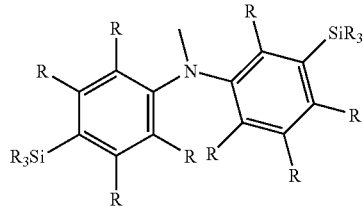
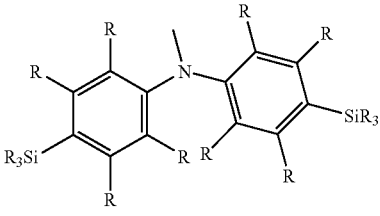
-continued
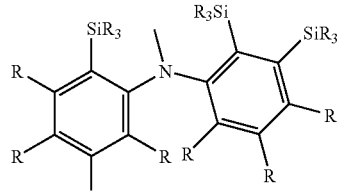
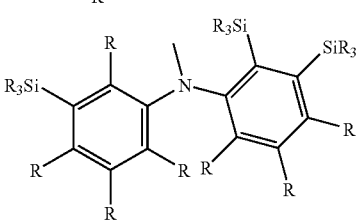
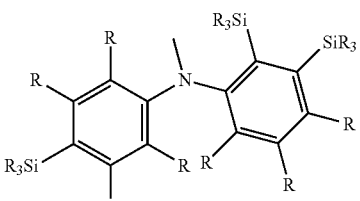
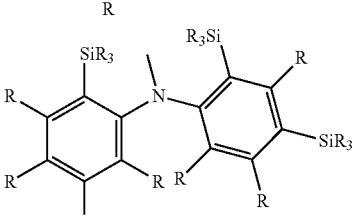
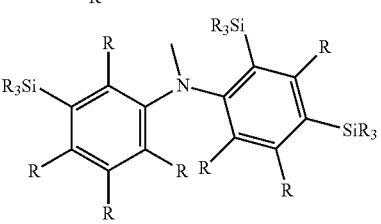
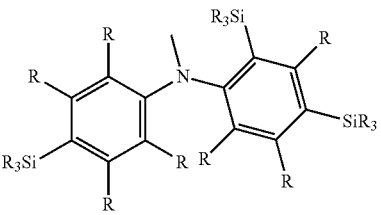
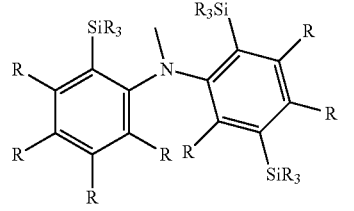
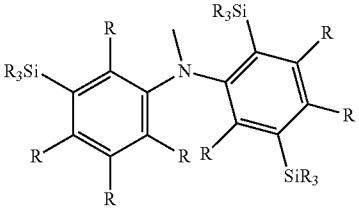

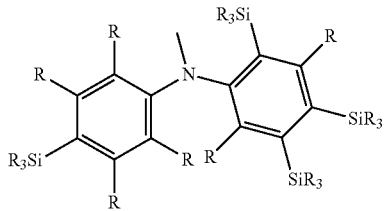
where R may comprise alkyl groups, alkoxy groups, aryl groups, alkenyl groups, arylene groups, or alkylene groups which are respectively independently H or C1 to C8,
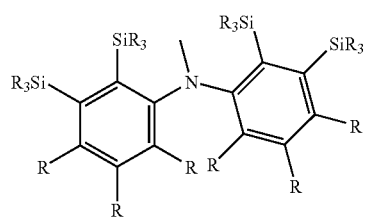
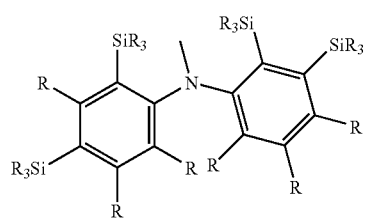
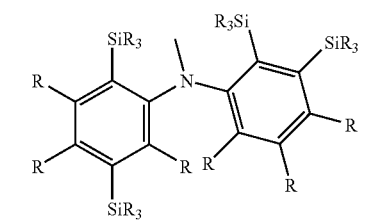
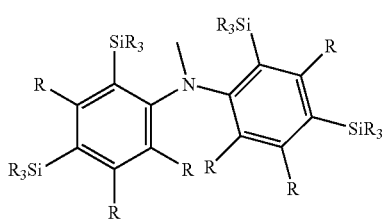
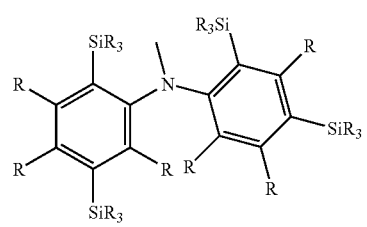
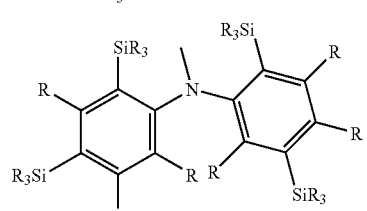
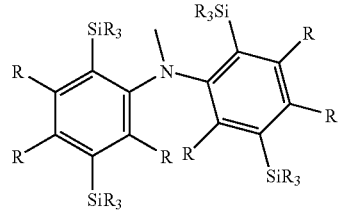
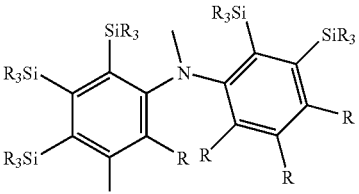
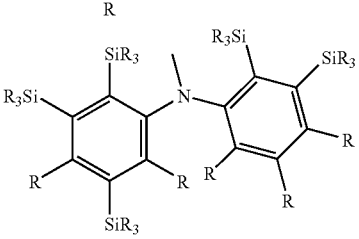
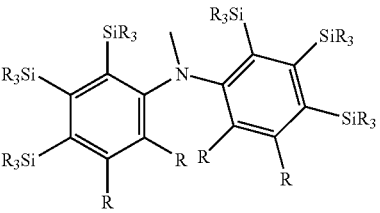
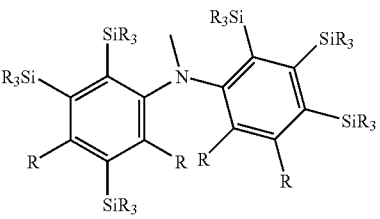
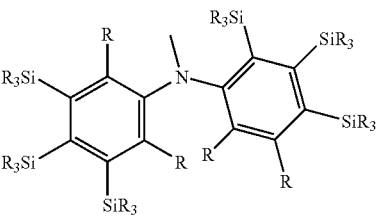
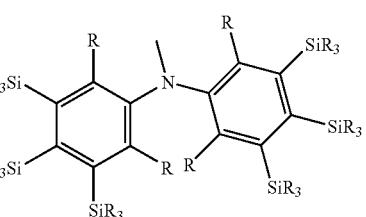
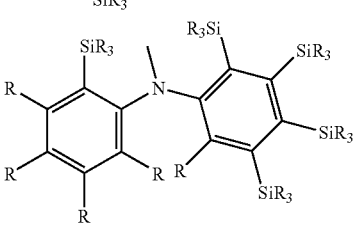

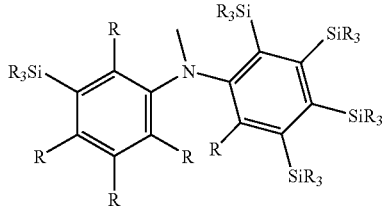
where R may comprise alkyl groups, alkoxy groups, aryl groups, alkenyl groups, arylene groups, or alkylene groups which are respectively independently H or C1 to C8,
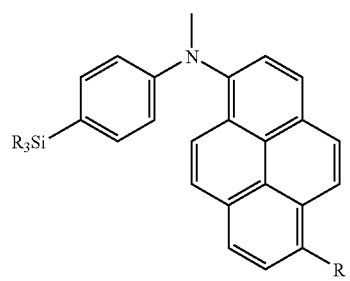
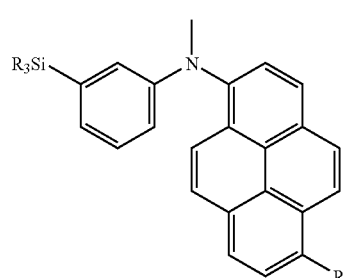
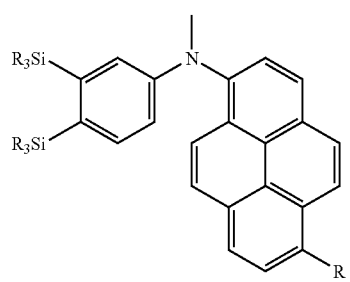
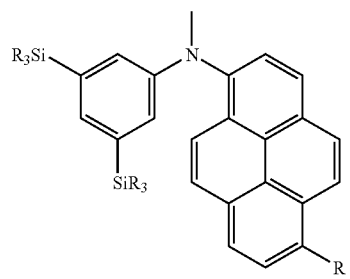
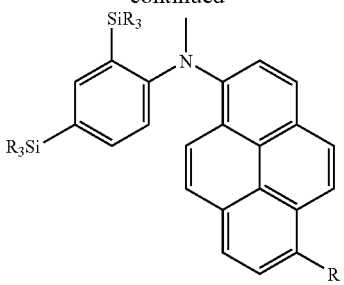
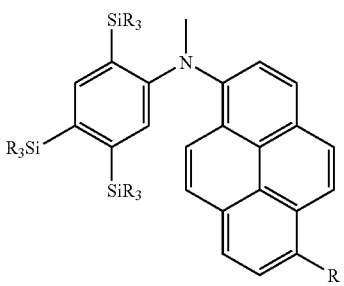
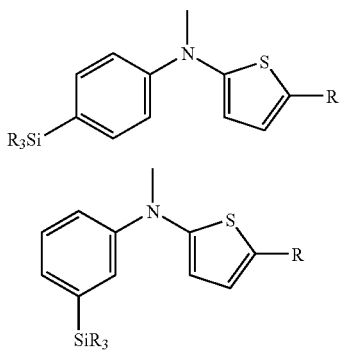
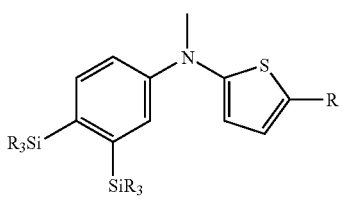
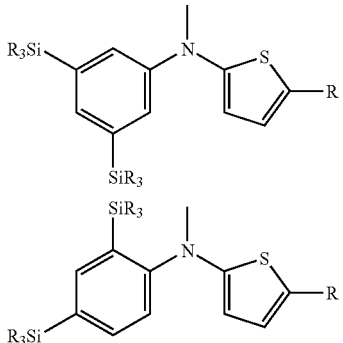
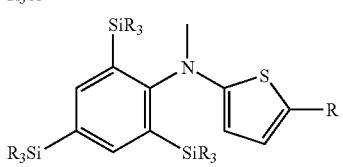
Here, R may comprise alkyl groups, alkoxy groups, aryl groups, alkenyl groups, arylene group, or alkylene groups which are respectively independently H or C1 to C8,

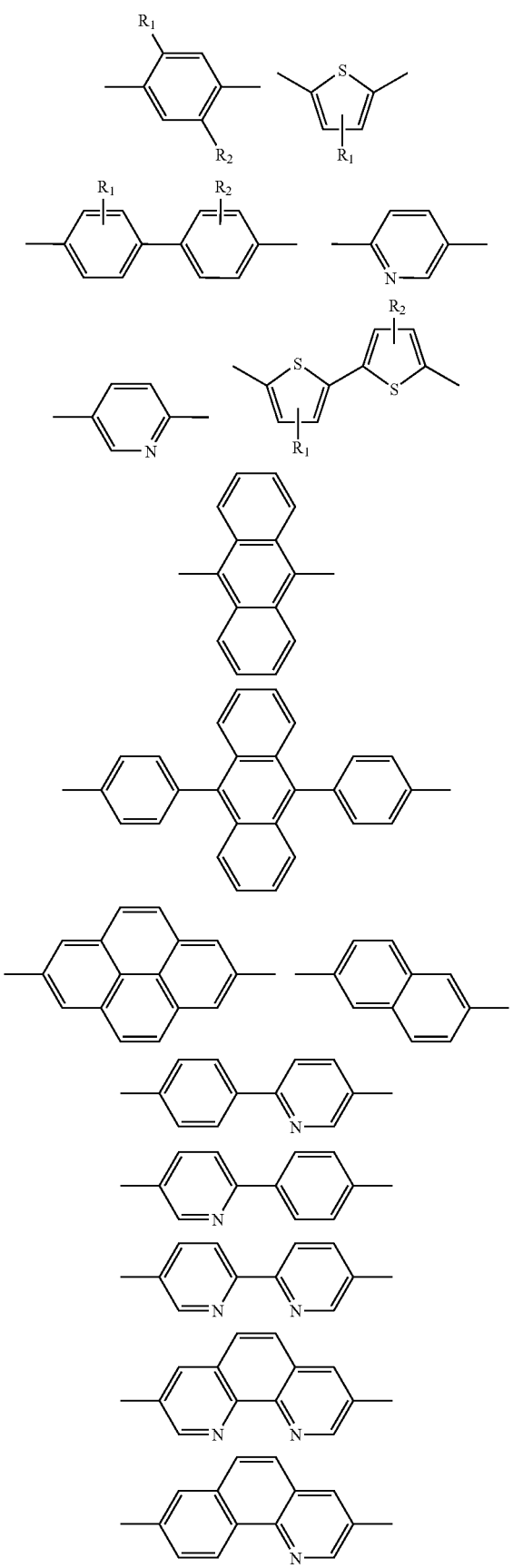

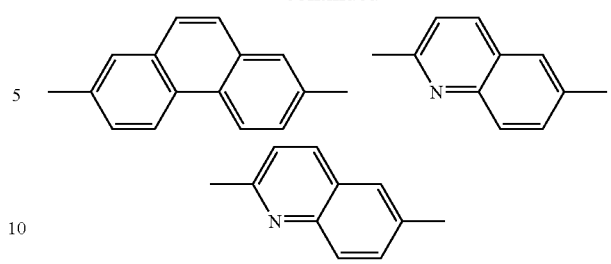

Here, $R_1$ and $R_2$ may comprise alkyl groups, alkoxy groups, aryl groups, alkenyl groups, arylene groups, or alkylene groups which are H or C1 to C8.

Hereinafter, some embodiments are described in order to help understanding of this document. However, the following embodiments only illustrate this document, and this document is not limited to the following embodiments.

Embodiment 1

Synthesis 1 of Dyes

Dyes for the dye-sensitized solar cell according to an embodiment of this document were synthesized through the following reactions.

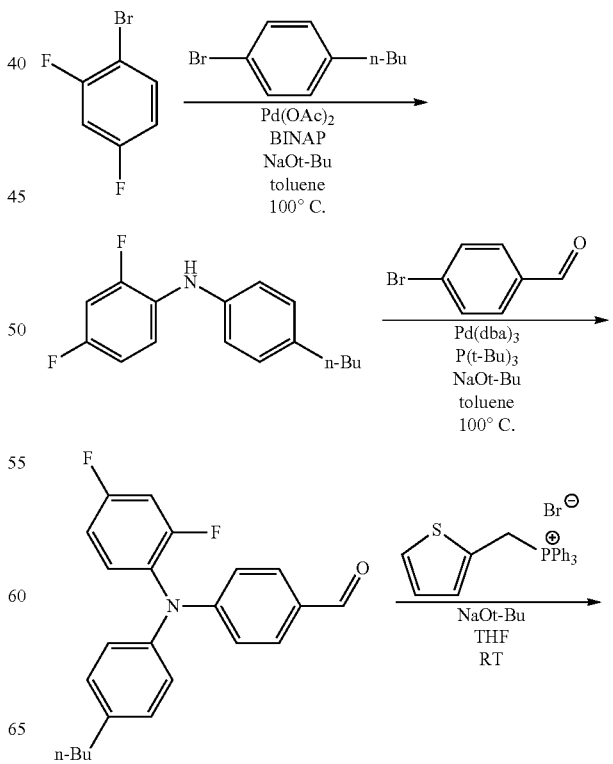

-continued

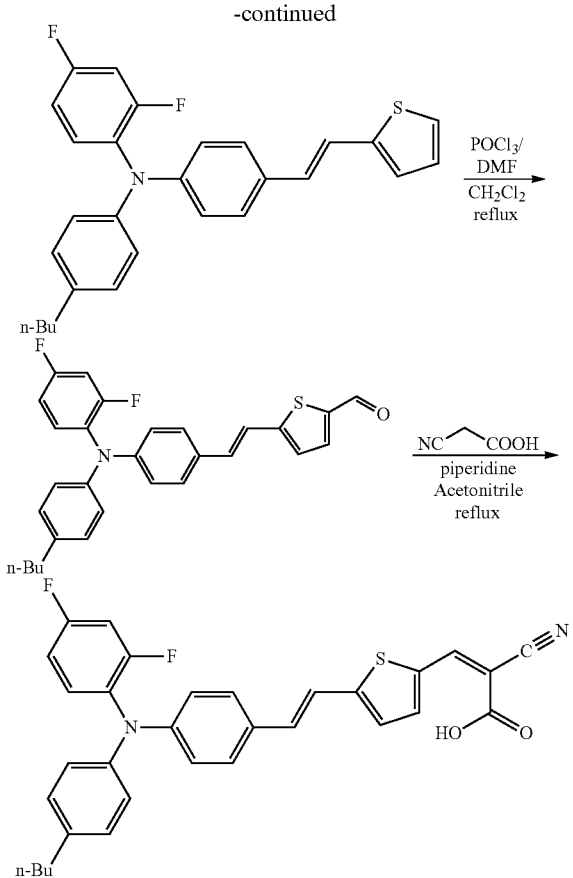

1) Fabrication of 4-butyl-N-(2,4-difluorophenyl)benzeneamine 2,4-difluoroaniline (44 m mol)), 1-bromo-4-butylbenzene (30 m mol)), palladium(II)acetate (0.4 m mol)), 2,2'-bis (diphenylphosphino)-1,1'-binaphthyl (0.9 m mol)), and potassium-tert-butoxide (44 m mol)) were dissolved in toluene (100 ml) in a 250 ml tri-neck-round bottom flask and then stirred in a bath of 100° C. for 24 hours. After the reaction was terminated, the toluene was removed from the solution. After extraction was performed on the solution using dichloromethane and water, the resulting solution was reduced in pressure and distilled. After a silica gel column chromatography, the solvent was reduced in pressure and distilled, thereby obtaining 4-butyl-N-(2,4-difluorophenyl)benzeneamine liquid having 0.3 g.

2) Fabrication of 4-(N-(4-butylphenyl)-N-(2,4-difluorophenyl)amino)benzaldehyde 4-butyl-N-(2,4-difluorophenyl)benzeneamine (30 m mol)), 4-bromobenzaldehyde (34 m mol)), tris(dibenzylideneaceton)dipalladium(O) (0.5 m mol)), tris-tert-butylphosphine (0.9 m mol)), and sodium-tert-butoxide (40 m mol)) were dissolved in toluene (100 ml) in a 250 ml tri-neck-round bottom flask and then stirred in a bath of 100° C. for 24 hours. After the reaction was terminated, the toluene was removed from the solution. After extraction was performed on the solution using dichloromethane and water, reduced pressure and distillation were performed on the resulting solution. After a silica gel column chromatography, the solvent was reduced in pressure and distilled, thereby obtaining 4-(N-(4-butylphenyl)-N-(2,4-difluorophenyl)amino)benzaldehyde liquid having 7.1 g.

3) Fabrication of N-(4-butylphenyl)-N-(2,4-difluorophenyl)-4-(-2-(thiophene-2-1)vinyl)benzeneamine Sodium-tert-butoxide (30 m mol)) was dissolved in anhydrous tetrahydrofuran (anhydrous THF) (100 ml) in a 250 ml tri-neck-round bottom flask on which a 100 ml-dropping funnel was mounted. 100 methyl triphenyl phosphonium salt (27 m mol)) was slowly added to the solution. When there was no more color change after the color of the solution was changed to a dark red color, 4-(N-(4-butylphenyl)-N-(2,4-difluorophenyl)amino)benzaldehyde was dissolved in anhydrous tetrahydrofuran (30 ml) and was then slowly dropped. After the resulting solution was stirred at room temperature for approximately 12 hours, the anhydrous tetrahydrofuran was removed from the solution. After a silica gel column was performed using dichloromethane and n-hexene, a solvent was reduced in pressure and was distilled. The resulting solution was recrystallized using dichloromethane and n-hexene and was then filtered, thereby obtaining N-(4-butylphenyl)-N-(2,4-difluorophenyl)-4-(-2-(thiophene-2-1)vinyl)benzeneamine solid having 8.4 g.

4) Fabrication of 5-(4-(N-(4-butylphenyl)-N-(2,4-difluorophenyl)amino)styryl)thiophene-2-carbaldehyde After DMF (5 ml) was dissolved in anhydrous methylene chloride (30 ml) in a 100 ml tri-neck-round bottom flask on which a 100 ml-dropping funnel was mounted, the flask was cooled to 0° C. using an ice bat and the solution was then stirred. Phosphorousoxychloride (26 m mol)) was slowly dropped to the cooled solution using an injector, stirred for 30 minutes, and then raised to room temperature. N-(4-butylphenyl)-N-(2,4-difluorophenyl)-4-(-2-(thiophene-2-1) vinyl) benzeneamine (17 m mol)) was dissolved in anhydrous methylenechloride (20 m ml) in a dropping funnel. The dissolved solution was injected and then slowly dropped to the solution using an injector. The resulting solution was heated up to a reflux temperature. The temperature of the solution was cooled in approximately 12 hours. A 2N sodium hydrooxide aqueous solution was dropped until it became neutral using pH paper. The solution was extracted using dichloromethane and water, and then reduced in pressure and distilled. After a silica gel column, the solvent was reduced in pressure and distilled, thereby obtaining 5-(4-(N-(4-butylphenyl)-N-(2,4-difluorophenyl)amino)styryl)thiophene-2-carbaldehyde solid having 3.5 g.

5) Fabrication of 3-(5-(4-(N-(4-butylphenyl)-N-(2,4-difluorophenyl)amino)styryl)thiophene-2-1)-2-cyanoacrylic acid 5-(4-(N-(4-butylphenyl)-N-(2,4-difluorophenyl)amino) styryl)thiophene-2-carbaldehyde (2.9 m mol)), 2-cyanoacetic acid (4.3 m mol)), and piperidine (7 m mol)) were dissolved in acetonitrile (50 ml) in a 100 ml tri-neck-round bottom flask and were then refluxed for 12 hours. After the reaction was terminated, the acetonitrile was removed from the solution. The solution was dissolved in a small amount of dichloromethane. After a silica gel column, a solvent was reduced in pressure and distilled. The solvent was precipitated in methanol and was then filtered, thereby obtaining 3-(5-(4-(N-(4-butylphenyl)-N-(2,4-difluorophenyl)amino) styryl)thiophene-2-1)-2-cyanoacrylic acid solid having 2.1 g.

Embodiment 2

Synthesis 2 of Dyes

Dyes for the dye-sensitized solar cell according to another embodiment of this document were synthesized through the following reactions.

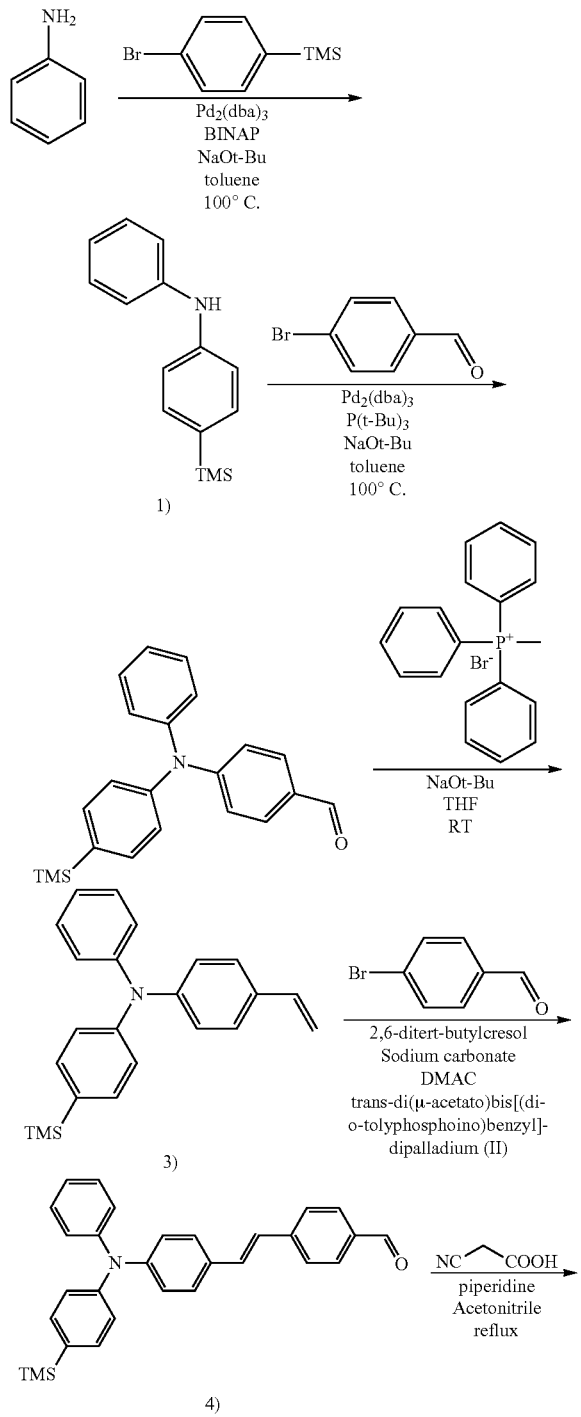

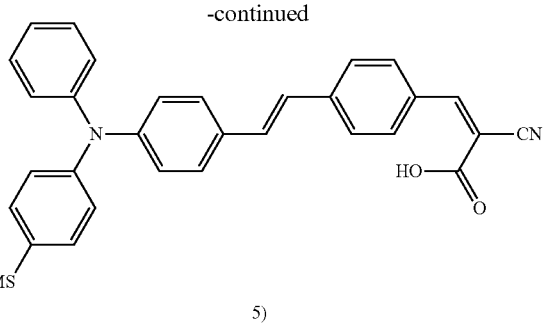

5)

(1) Fabrication of 4-(trimethylsilyl)-N-phenylbenzeneamine

Aniline (127.5 m mol)), (4-bromophenyl)trimethylsilane (102 m mol)), tris(dibenzylideneaceton)dipalladium(O) (1.53 m mol)), BINAP(2,2'-bis(diphenylphosphino)-1,1'-binaphthyl (3.06 m mol)), and sodium-tert-butoxide (132.6 m mol)) were dissolved in toluene (100 ml) in a 250 ml tri-neck-round bottom flask and then stirred in a bath of 100° C. for 24 hours. After the reaction was terminated, the toluene was removed from the solution. After extraction was performed on the solution using dichloromethane and water, the resulting solution was reduced in pressure and distilled. After a silica gel column chromatography, the solvent was reduced in pressure and distilled, thereby obtaining 4-(trimethylsilyl)-N-phenylbenzeneamine liquid having 0.3 g.

(2) Fabrication of 4-(N-(4-(trimethylsilyl)phenyl)-N-phenylamino)benzaldehyde 4-(trimethylsilyl)-N-phenylbenzeneamine (22.8 m mol)), 4-bromobenzaldehyde (29.64 m mol)), tris(dibenzylideneaceton)dipalladium(O) (0.342 m mol)), tris-tert-butyl phosphine (0.684 m mol)), and sodium-tert-butoxide (29.64 m mol)) were dissolved in toluene (100 ml) in a 250 ml tri-neck-round bottom flask and were then stirred in a bath of 100° C. for 24 hours. After the reaction was terminated, the toluene was removed from the solution. After extraction was performed on the solution using dichloromethane and water, the resulting solution was reduced in pressure and distilled. After a silica gel column chromatography, the solvent was reduced in pressure and distilled, thereby obtaining 4-(N-(4-(trimethylsilyl)phenyl)-N-phenylamino)benzaldehyde liquid having 4.1 g.

(3) Fabrication of N-(4-(trimethylsilyl)phenyl)-N-phenyl-4-vinylbenzeneamine

Sodium-tert-butoxide (19 m mol)) was dissolved in anhydrous tetrahydrofuran (anhydrous THF) (100 ml) in a 250 ml tri-neck-round bottom flask on which a 100 ml-dropping funnel was mounted. Methyltriphenylphosphoniumbromide (17.8 m mol)) was then slowly added to the solution. When there was no more color change after the color of the solution was changed to a dark yellow color, N-(4-(trimethylsilyl) phenyl)-N-phenyl-4-vinylbenzeneamine was dissolved in anhydrous tetrahydrofuran (30 ml) and was then slowly dropped. After stirring at room temperature for approximately 12 hours, the anhydrous tetrahydrofuran was removed from the solution. After a silica gel column was performed using dichloromethane and n-hexane, a solvent was reduced in pressure and was distilled, thereby obtaining N-(4-trimethylsilyl)phenyl)-N-phenyl-4-vinylbenzeneamine solid having 3.0 g.

(4) Fabrication of N-((4-(trimethylsilyl)phenyl)-N-phenyl-4-(4-aminostyryl)benzaldehyde N-(4-trimethylsilyl)phenyl)-N-phenyl-4-vinylbenzeneamine (8.7 m mol), 4-bromobenzaldehyde (17.4 m mol), 2,6-ditert-butylcresol (0.87 m mol), sodium-tert-butoxide (9.57 m mol), and trans-di(μ-acetato)bis[(di-o-tolyphosphoino)benzyl]-dipalladium(II) (0.087 m mol) were dissolved in N,N-dimethylaceteamide (50 ml) in a 100 ml two-neck-round bottom flask and then stirred in a bath of 80° for 24 hours. After the reaction was terminated, the solution was glass-filtered using a silica gel and sellaite. The N,N-dimethylaceteamide was removed using reduction pressure and distillation. Next, after a silica gel column was performed using dichloromethane and n-hexene, a solvent was reduced in pressure and distilled, thereby obtaining N-((4-trimethylsilyl)phenyl)-N-phenyl-4-(4-aminostyryl)benzaldehyde solid having 1.9 g.

(5) Fabrication of N-((4-trimethylsilyl)phenyl)-N-phenyl-4-((4-aminostyryl)-2-cyano)-3-phenylacrylic acid N-((4-trimethylsilyl)phenyl)-N-phenyl-4-(4-aminostyryl)benzaldehyde (4.2 m mol), 2-cyanoacetic acid (6.3 m mol), and piperidine (10.5 m mol) were dissolved in acetonitrile (50 ml) in a 100 ml two-neck-round bottom flask and then refluxed for 12 hours. After the reaction was terminated, the acetonitrile was removed. After a silica gel column is performed using dichloromethane and methanol, a solvent was reduced in pressure and distilled. The result was then precipitated in methanol and distilled, thereby obtaining N-((4-trimethylsilyl)phenyl)-N-phenyl-4-((4-aminostyryl)-2-cyano)-3-phenylacrylic acid solid having 2.1 g.

Embodiment 3

Fabrication of Dye-Sensitized Solar Cell (1) Fabrication of Task Electrode

FTO glass (fluorine-doped tin oxide coated conduction glass, Pilkington, TEC7) was cut to have a size of 1.5 cm×1.5 cm. The cut glass was washed using a glass cleaning detergent through ultrasonic decomposition washing for 10 minutes. Soap water was completely removed from the FTO glass using distilled water. The FTO glass was then washed twice using ethanol through ultrasonic decomposition washing for 15 minutes. The resulting FTO glass was sufficiently rinsed using anhydrous ethanol and then dried in an oven of 100° C. In order to improve contact force with $TiO_2$, the FTO glass was dipped in a titanium(IV) chloride solution (40 mM) in a temperature of 70° C. for 40 minutes and was then washed using distilled water. The FTO glass was sufficiently dried in an oven of 100° C. Next, titanium dioxide ($TiO_2$) paste (18-NR, available from CCIC Corporation) was coated on the FTO glass using a screen printer in the form of a 9 mm×9 mm mask (200 meshes). The coated film was dried in an oven of 100° C. for 20 minutes. The above process was repeatedly performed three times. The coated film was then cured in a temperature of 450° C. for 60 minutes, thereby obtaining a $TiO_2$ film of approximately 10 μm in thickness. The $TiO_2$ film on which an annealing process was performed was dipped in an anhydrous ethanol solution of synthesized dyes having a concentration of 0.5 mM for 24 hours so that the dyes could be adsorbed to the $TiO_2$ film. (In the case where the dyes are not dissolved in the anhydrous ethanol solution, a solvent capable of dissolving the dyes may be used) After the adsorption was finished, the dyes that were not adsorbed by the anhydrous ethanol solution were completely washed and then dried using a heat gun.

(2) Fabrication of Counter Electrode

Two holes into which an electrolyte would enter were perforated into the FTO glass of 1.5 cm×1.5 cm in size using a φ0.7 mm—diamond drill (Dremel multipro395). The FTO glass was washed using the same washing method as that presented in the task electrode and was then dried. Next, a hydrogenhexachloroplatinum($H_2PtCl_6$)2-propanol solution was coated on the FTO glass and then cured in a temperature of 450° for 60 minutes.

(3) Fabrication of Sandwitch Cell

A surlyn (SX1170-25 Hot Melt), cut to have a square belt shape, was placed between the task electrode and the counter electrode. The two electrodes were coalesced each other using a clip and an oven. An electrolyte was injected into the coalesced electrodes through the two small holes of the counter electrode. The resulting electrodes were sealed using a surlyn strip and cover glass, thereby fabricating a sandwitch cell. In this case, the electrolyte solution was fabricated using 0.1M LiI, 0.05M $1_2$, 0.6M 1-hexyl-2,3-dimethylimideazoliumiodide, and 0.5M 4-tert-butylpyridine as a 3-methoxypropionitrile solvent.

(4) Measurement of Photocurrent-Voltage

A current-voltage curve was obtained using an M236 source measure unit (SMU, available from Keithley Instruments Inc.) by irradiating light to the above-fabricated sandwitch cell using a Xe lamp (Oriel 300 W Xe arc lamp, available from Newport Corporation) on which an AM 1.5 solar simulating filter was mounted. The range of potential was from −0.8 V to 0.2 V, and the intensity of light was 100 mW/cuff.

Experimental examples in which the respective solar cells fabricated according to the above-described embodiments were fabricated are described below.

Experimental Example 1

A solar cell was fabricated using dyes having the following chemical structure 2.

[Chemical Structure 2]

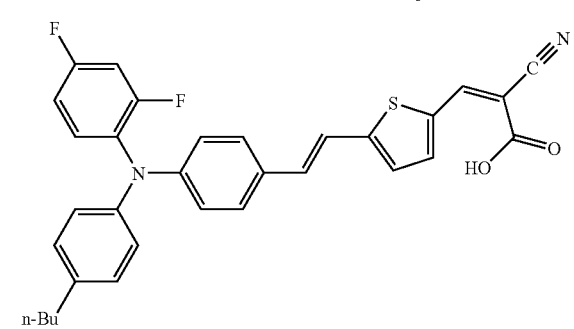

Experimental Example 2

A solar cell was fabricated using dyes having the following chemical structure 3.

[Chemical Structure 3]

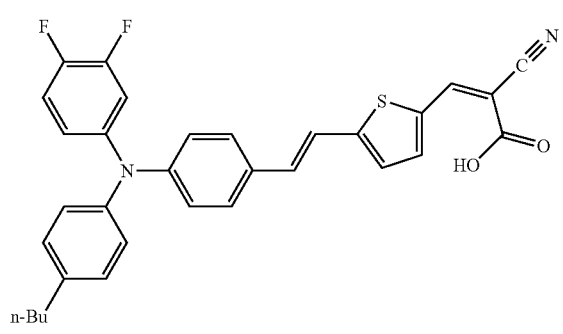

Experimental Example 3

A solar cell was fabricated using dyes having the following chemical structure 4.

[Chemical Structure 3]

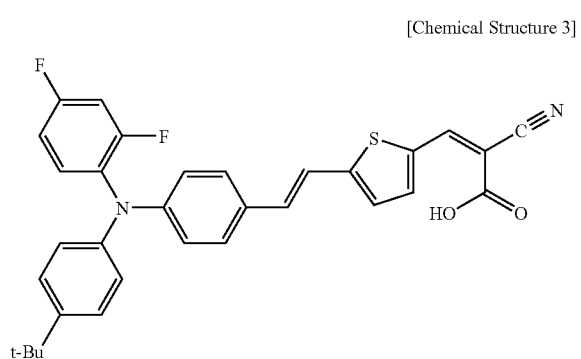 [SMILES: CC(C)(C)c1ccc(N(c2ccc(/C=C/c3ccc(/C=C(/C#N)C(=O)O)s3)cc2)c2ccc(F)cc2F)cc1]

Experimental Example 4

A solar cell was fabricated using dyes having the following chemical structure 5.

[Chemical Structure 5]

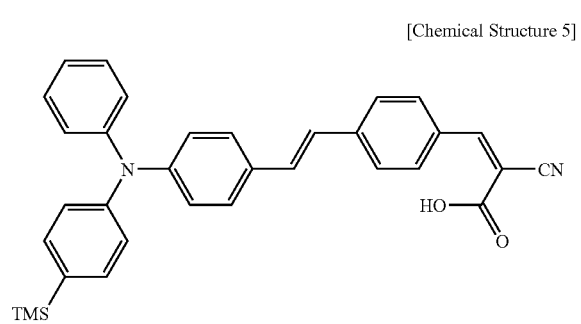 [SMILES: C[Si](C)(C)c1ccc(N(c2ccccc2)c2ccc(/C=C/c3ccc(/C=C(/C#N)C(=O)O)cc3)cc2)cc1]

Experimental Example 5

A solar cell was fabricated using dyes having the following chemical structure 6.

[Chemical Structure 6]

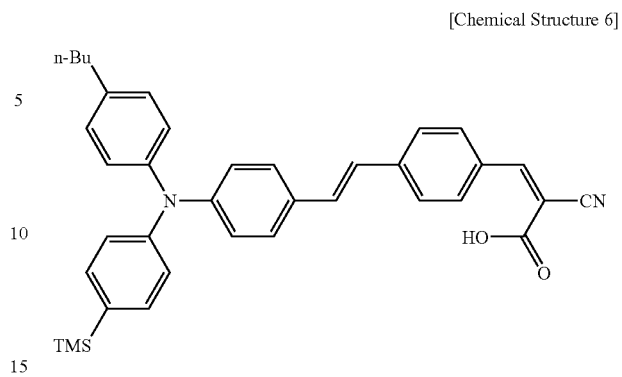

Experimental Example 6

A solar cell was fabricated using dyes having the following chemical structure 7.

[Chemical Structure 7]

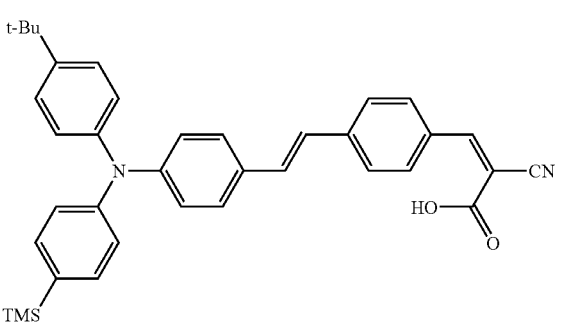

Comparison Example

A solar cell was fabricated using dyes having the following chemical structure 8.

[Chemical Structure 8]

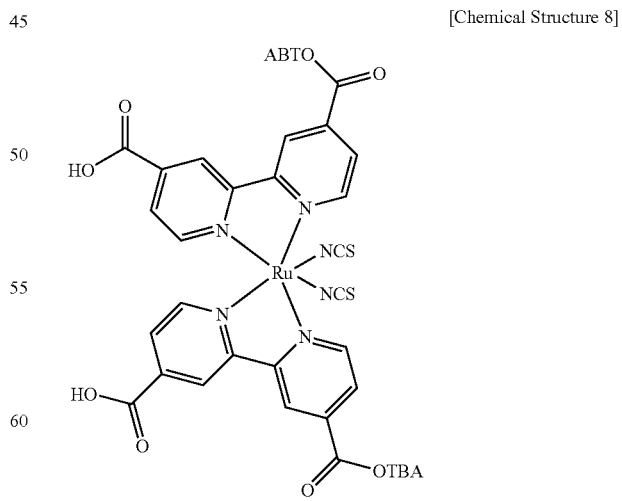

$J_{sc}$ (a short-circuit photocurrent density), $V_{oc}$ (an open circuit voltage), FF(a fill factor), and a photoelectric conversion efficiency (PCE) of each of the dye-sensitized solar cells fabricated according to the experimental examples 1 to 6 and the comparison example were measured and listed in the following table 1. Here, the above measurements for each of the experimental examples and the comparison example were performed twice under the same condition.

TABLE 1

|  | # | Area (cm$^2$) | $J_{sc}$ (mA) | $V_{oc}$ (V) | FF (%) | PCB (%) |
|---|---|---|---|---|---|---|
| Experimental example 1 | 1 | 0.266 | 12.73 | 0.634 | 72.32 | 5.85 |
|  | 2 | 0.272 | 12.97 | 0.644 | 70.34 | 5.87 |
| Experimental example 2 | 1 | 0.275 | 12.14 | 0.650 | 71.88 | 5.67 |
|  | 2 | 0.270 | 12.31 | 0.655 | 71.16 | 5.74 |
| Experimental example 3 | 1 | 0.271 | 11.29 | 0.630 | 70.62 | 5.03 |
|  | 2 | 0.272 | 11.96 | 0.658 | 72.45 | 5.70 |
| Experimental example 4 | 1 | 0.271 | 12.10 | 0.625 | 70.02 | 5.30 |
|  | 2 | 0.270 | 12.32 | 0.653 | 71.23 | 5.73 |
| Experimental example 5 | 1 | 0.274 | 12.42 | 0.648 | 71.56 | 5.76 |
|  | 2 | 0.273 | 12.57 | 0.646 | 71.41 | 5.80 |
| Experimental example 6 | 1 | 0.272 | 11.78 | 0.652 | 71.29 | 5.47 |
|  | 2 | 0.275 | 11.81 | 0.671 | 72.71 | 5.76 |
| Comparison Example | 1 | 0.270 | 16.21 | 0.755 | 71.40 | 8.73 |
|  | 2 | 0.270 | 15.90 | 0.779 | 71.90 | 8.90 |

From the above table 1, it can be seen that each of the solar cells fabricated according to the experimental examples 1 to 6 of this document has the open circuit voltage ($V_{oc}$) comparable to that of the comparison example and also has the photoelectric conversion efficiency (PCE), which is 80% of that of the comparison example using dyes (N719) having the highest efficiency today.

Accordingly, the dyes for a dye-sensitized solar cell and the solar cell including the same according to the embodiments of this document are advantageous in that they can be fabricated much cheaply when compared with conventional organic metallic solar cells, but can be fabricated to have a photoelectric conversion efficiency comparable to that of the conventional organic metallic solar cells, and can also be fabricated to have a longer lifespan than that of organic metallic dyes.

While this document has been described in connection with what is presently considered to be practical exemplary embodiments, it is to be understood that this document is not limited to the disclosed embodiments, but, on the contrary, is intended to cover various modifications and equivalent arrangements included within the spirit and scope of the appended claims.

What is claimed is:

1. Dyes for a dye-sensitized solar cell, each of the dyes having the following chemical structure 1;

[Chemical Structure 1]

wherein each of X and Y consists of a substituent, comprising aromatic hydrocarbon groups which are respectively independently substituted or unsubstituted, aromatic heterocyclic groups which are substituted or unsubstituted, and a combination thereof, Z consists of aromatic hydrocarbon groups which are substituted or unsubstituted, heterocyclic groups which are substituted or unsubstituted, vinyl groups, and polyvinyl groups which are substituted or unsubstituted, and A consists of acid functional groups, wherein at least one of the X and Y consists of silane derivatives substituted with alkyl groups or aryl groups.

2. The dyes for a dye-sensitized solar cell of claim 1, wherein:

each of the X and Y consists of a substituent, comprising aromatic hydrocarbon groups which are configured to have the number of carbons of 5 to 20 and are independently substituted or unsubstituted, aromatic heterocyclic groups which are substituted or unsubstituted, and a combination thereof, and at least one of the X and Y consists of silane derivatives substituted with alkyl groups, alkoxy groups, aryl groups, alkenyl groups, arylene groups, and alkylene groups.

3. The dyes for a dye-sensitized solar cell of claim 1, wherein each of the X and Y consists of a substituent selected from the group consisting of alkyl, alkoxy, aryl groups, arylene groups, alkylene groups, and a combination thereof.

4. The dyes for a dye-sensitized solar cell of claim 1, wherein the Z consists of a substituent selected from the group consisting of thiophene, vinyl groups, polyvinyl groups, benzene, naphthalene, antracence, fluorene, biphenyl, pyran, pyrrole, carbazole, and a combination thereof.

5. The dyes for a dye-sensitized solar cell of claim 1, wherein the Z consists of a substituent selected from the group consisting of alkyl, alkoxy, aryl groups, alkenyl groups, arylene groups, alkylene groups, and a combination thereof.

6. The dyes for a dye-sensitized solar cell of claim 1, wherein the A consists of a substituent selected from the group consisting of carboxy acid groups, phosphorous acid groups, sulfon acid groups, phosphinic acid groups, hydroxy acid groups, oxycarboxy acids, and a combination thereof.

7. The dyes for a dye-sensitized solar cell of claim 1, wherein the X—N—Y consists of any one of the following compounds:

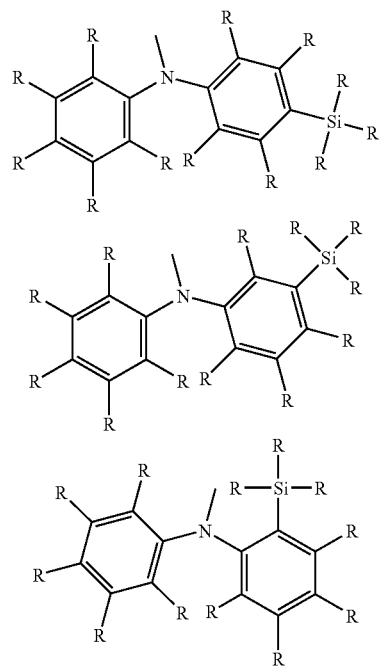

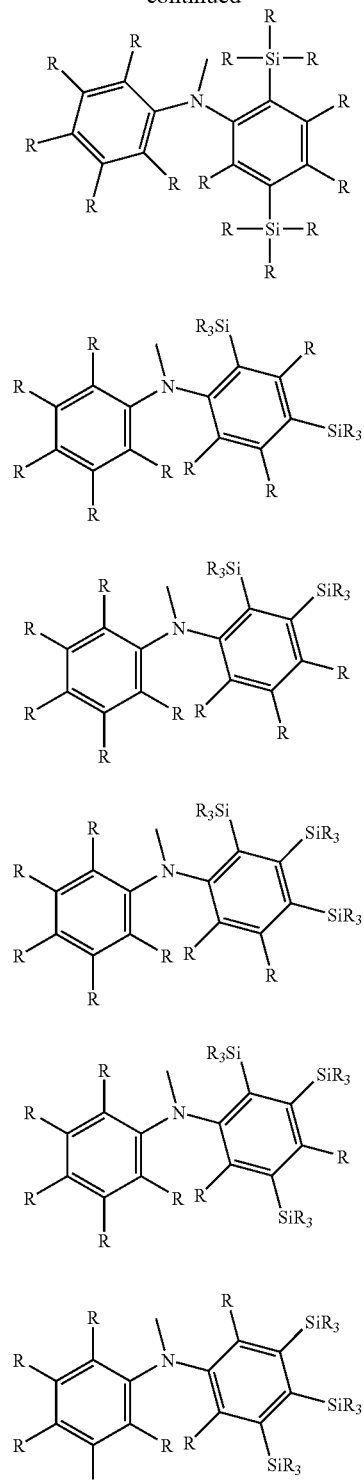
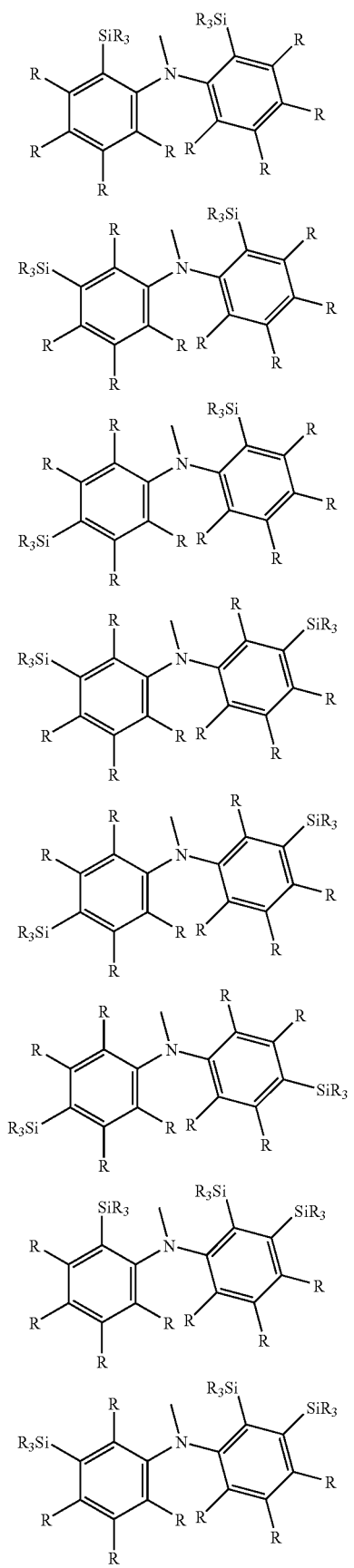
where R is independently selected from the group consisting of an alkyl group, an alkoxy group, an aryl group, an alkenyl group, an arylene group, and an alkylene group which is configured to have the number of carbons of 1 to 8, or where R independently is H, -continued
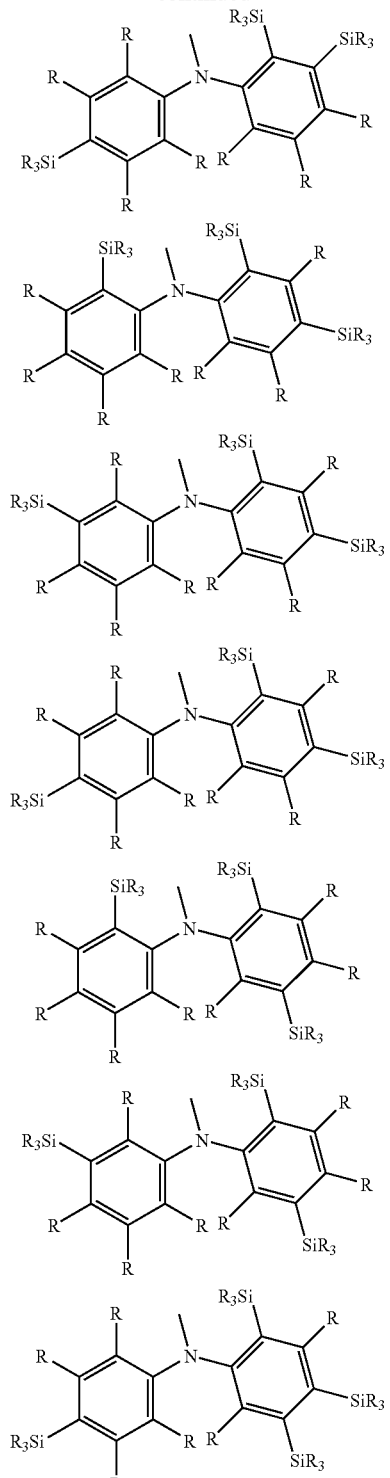
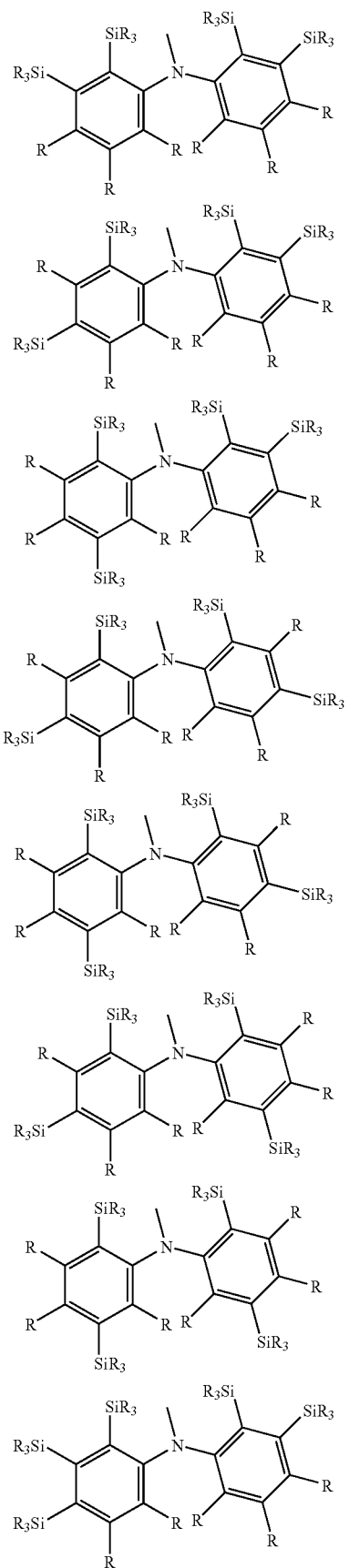
where R is independently selected from the group consisting of an alkyl group, an alkoxy group, an aryl group, an alkenyl group, an arylene group, and an alkylene group which is configured to have the number of carbons of 1 to 8, or where R independently is H,

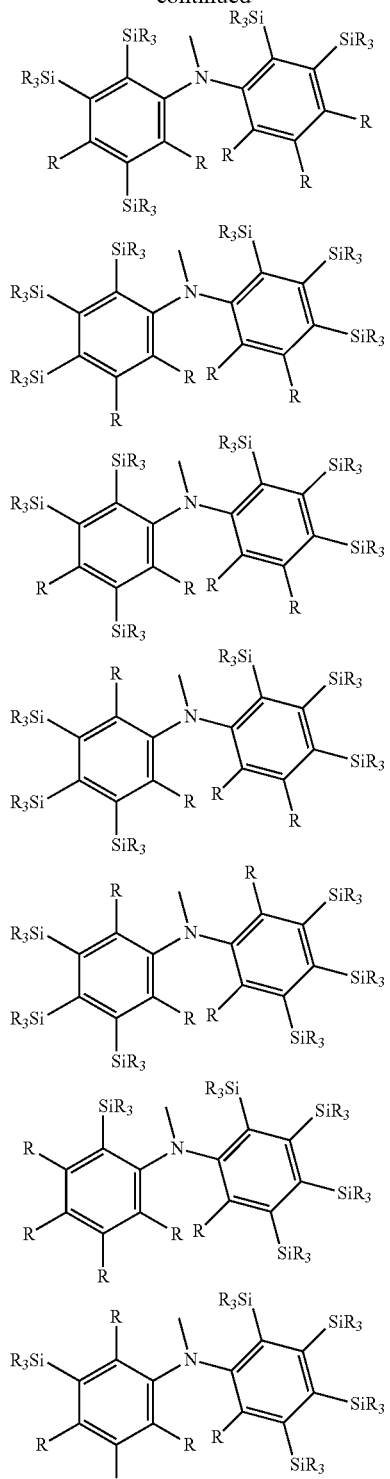
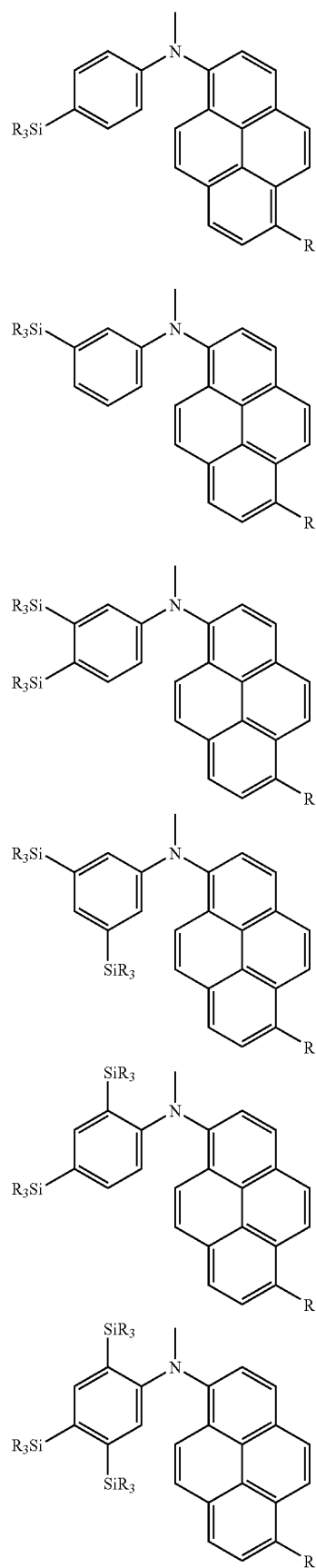
where R is independently selected from the group consisting of an alkyl group, an alkoxy group, an aryl group, an alkenyl group, an arylene group, and an alkylene group which is configured to have the number of carbons of 1 to 8, or where R independently is H, -continued

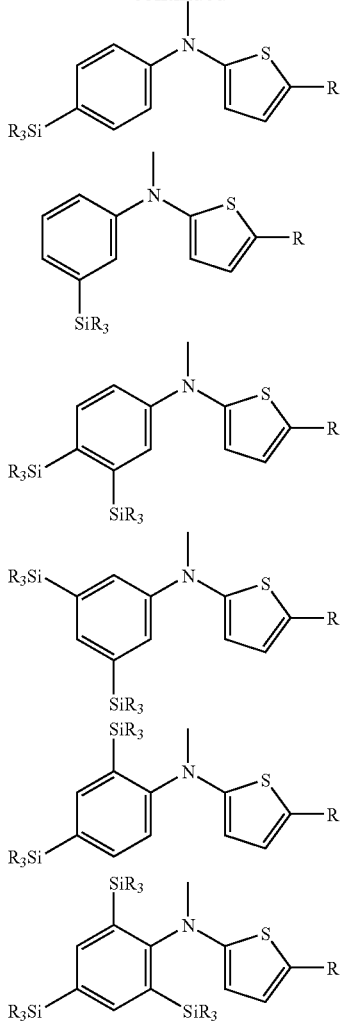

where R is independently selected from the group consisting of an alkyl group, an alkoxy group, an aryl group, an alkenyl group, an arylene group, and an alkylene group which is configured to have the number of carbons of 1 to 8, or where R independently is H,

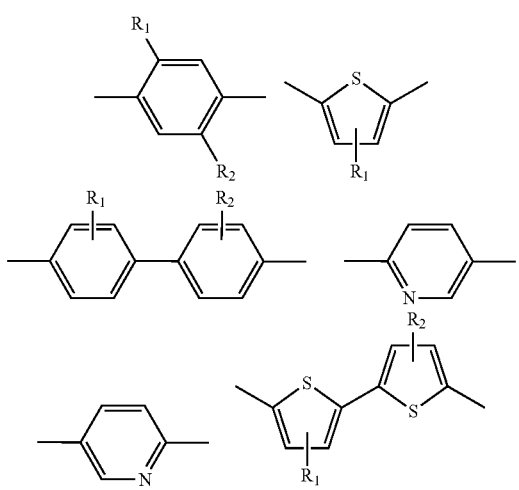

-continued

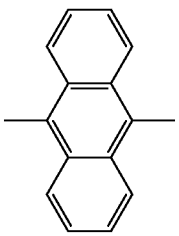

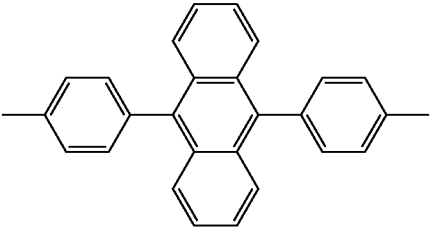

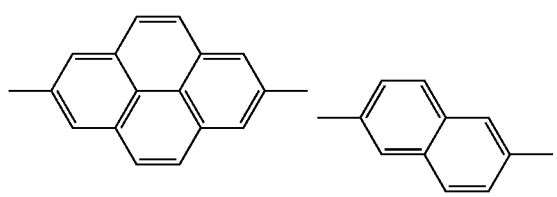

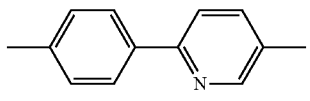

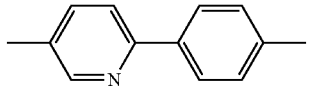

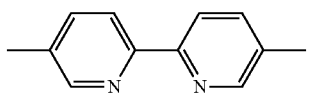

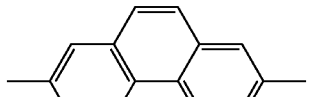

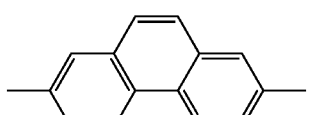

where R is independently selected from the group consisting of an alkyl group, an alkoxy group, an aryl group, an alkenyl group, an arylene group, and an alkylene group which is configured to have the number of carbons of 1 to 8, or where R independently is H.

* * * * *